United States Patent
Chauhan et al.

(10) Patent No.: US 11,526,876 B2
(45) Date of Patent: Dec. 13, 2022

(54) SYSTEM FOR CALIBRATION OF AN EEG DEVICE FOR DETECTION OF SPECIFIC BRAINWAVE PATTERNS

(71) Applicant: Bank of America Corporation, Charlotte, NC (US)

(72) Inventors: Sandeep Kumar Chauhan, Hyderabad (IN); Ravi Kumar Kesani, Hyderabad (IN)

(73) Assignee: BANK OF AMERICA CORPORATION, Charlotte, NC (US)

( * ) Notice: Subject to any disclaimer, the term of this patent is extended or adjusted under 35 U.S.C. 154(b) by 269 days.

(21) Appl. No.: 16/925,012

(22) Filed: Jul. 9, 2020

(65) Prior Publication Data
US 2022/0013221 A1    Jan. 13, 2022

(51) Int. Cl.
G06Q 20/38 (2012.01)
G06Q 40/02 (2012.01)
G06F 3/01 (2006.01)
G06Q 20/40 (2012.01)
G06Q 30/00 (2012.01)
H04L 9/40 (2022.01)

(52) U.S. Cl.
CPC ......... *G06Q 20/382* (2013.01); *G06F 3/015* (2013.01); *G06Q 20/40145* (2013.01); *G06Q 30/0185* (2013.01); *G06Q 40/02* (2013.01); *H04L 63/083* (2013.01)

(58) Field of Classification Search
CPC ...... G06F 3/015; G06Q 20/382; H04L 63/083
USPC ........................................................ 713/186
See application file for complete search history.

(56) References Cited

U.S. PATENT DOCUMENTS

| 8,799,670 | B2 | 8/2014 | Naccache |
| 9,438,591 | B2 | 9/2016 | Hama |
| 9,532,748 | B2 | 1/2017 | Denison et al. |
| 9,654,468 | B2 | 5/2017 | Buer |
| 9,814,426 | B2 | 11/2017 | Connor |
| 9,968,297 | B2 | 5/2018 | Connor |
| 10,234,942 | B2 * | 3/2019 | Connor ............... A61B 5/6814 |
| 10,291,977 | B2 | 5/2019 | Mackellar et al. |
| 10,345,902 | B1 | 7/2019 | Yildiz et al. |
| 10,449,359 | B2 * | 10/2019 | Kahana ............. A61N 1/36064 |
| 10,607,507 | B2 | 3/2020 | Connor |
| 10,638,965 | B2 * | 5/2020 | Flax ....................... G16H 50/20 |
| 10,813,619 | B2 | 10/2020 | Samec et al. |
| 2016/0004862 | A1 | 1/2016 | Almehmadi et al. |
| 2018/0012009 | A1 | 1/2018 | Furman et al. |
| 2018/0137358 | A1 | 5/2018 | Rousseau et al. |

(Continued)

FOREIGN PATENT DOCUMENTS

RU    2736707 C1    11/2020
RU    2736709 C1    11/2020

(Continued)

*Primary Examiner* — Calvin C Ma
(74) *Attorney, Agent, or Firm* — Moore & Van Allen PLLC; Nicholas C. Russell

(57) ABSTRACT

Embodiments of the invention are directed to a system, method, and computer program product for calibrating a brain activity morning system. The system may receive a transmission that indicates a user desires to calibrate a brain activity measuring device. The system may determine a calibration procedure appropriate for the user. The system can also store one or more settings based on the calibration procedure.

20 Claims, 8 Drawing Sheets

(56) References Cited

U.S. PATENT DOCUMENTS

| | | |
|---|---|---|
| 2018/0285540 A1 | 10/2018 | Chen et al. |
| 2018/0292902 A1 | 10/2018 | Min |
| 2019/0377859 A1 | 12/2019 | Chen et al. |
| 2020/0151308 A1 | 5/2020 | Phillips |
| 2020/0151474 A1 | 5/2020 | Zandi et al. |
| 2020/0201974 A1 | 6/2020 | Xiong |
| 2022/0129534 A1 | 4/2022 | Croxford et al. |

FOREIGN PATENT DOCUMENTS

| | | |
|---|---|---|
| RU | 2736710 C1 | 11/2020 |
| RU | 2736711 C1 | 11/2020 |
| RU | 2736804 C1 | 11/2020 |

\* cited by examiner

SYSTEM FOR CALIBRATION OF AN EEG DEVICE FOR DETECTION OF SPECIFIC BRAINWAVE PATTERNS

FIELD OF THE INVENTION

The present invention is directed to, in general, a novel, proactive approach for wireless communication between a brain activity monitoring system and a resource. Specifically, embodiments of the present invention are directed to utilizing brain activity signals received from a user to perform one or more actions associated with the resource.

BACKGROUND

Historically, people have interacted with resources, such as a bank, via in person transactions. For example, a person may enter into a physical building associated with the resource and personally interact with personnel associated with the resource, or physically interact with an automated machine, to complete a transaction. However, people may prefer to avoid interacting with personnel or physically interacting with the automated machines. Accordingly, there is a need for systems and methods that assist people with contactless transactions, such as wirelessly communicating between a brain activity monitoring system and a resource, in order to reduce in person or physical contact with the user.

The previous discussion of the background to the invention is provided for illustrative purposes only and is not an acknowledgement or admission that any of the material referred to is or was part of the common general knowledge at the priority date of the application.

SUMMARY

In one aspect, the present disclosure is directed to a system for wireless communication between a brain activity monitoring system and a resource. In one embodiment, the system can comprise at least one memory device; at least one communication device connected to a communications network; at least one processing device operatively coupled to the at least one memory device; and a module stored in the at least one memory device comprising executable instructions. The executable instructions, that when executed by the at least one processing device, can cause the at least one processing device to transmit, based on determining that a user is utilizing a brain activity measuring device associated with a resource application, a request for a password associated with a resource account associated with the user. The executable instructions can also cause the at least one processing device to receive a first brain activity signal that indicates the user's response to the request for the password. The executable instructions can also cause the at least one processing device to determine, based on the first brain activity signal, that the first brain activity signal indicates the password associated with the resource account. The executable instructions can also cause the at least one processing device to transmit a notification that indicates confirmation that the first brain activity signal indicated the password associated with the resource account and indicates a request for a transaction that the user desires to complete. The executable instructions can also cause the at least one processing device to receive, based on transmitting the notification, a second brain activity signal that indicates a resource transaction that the user desires to complete. The executable instructions can also cause the at least one processing device to determine, based on the second brain activity signal, the resource transaction that the user desires to complete. The executable instructions can also cause the at least one processing device to transmit, based on the determined resource transaction that the user desires to complete, a request that the user confirm that the determined resource transaction is the resource transaction that the user desires to complete. The executable instructions can also cause the at least one processing device to execute, based on receiving a third brain activity signal that indicates the determined resource transaction is the resource transaction that the user desires to complete, the resource transaction.

In another embodiment, and in combination with any of the previous embodiments, the brain activity measuring device can be configured to communicate with the at least one processing device via a first networked device associated with the user, and wherein the brain activity measuring device is configured to measure electroencephalogram (EEG) signals associated with the user.

In another embodiment, and in combination with any of the previous embodiments, the executable instructions further cause the at least one processing device to: receive a fourth brain activity signal associated with the user; determine that the fourth brain activity signal that is associated with brain activity that is undeterminable; transmit a notification that indicates the fourth brain activity signal is associated with brain activity that is undeterminable; and receive, in response to transmitting the notification, a fifth brain activity signal that is determinable.

In another embodiment, and in combination with any of the previous embodiments, the executable instructions that cause the at least one processing device to execute the resource transaction further cause the processing device to: determine that the resource transaction is associated with the user desiring assistance from personnel associated with a resource network; transmit, to a device associated with the resource network, a notification that indicates that the user desires assistance from the personnel associated with the resource network; and transmit to the first networked device a notification that the personnel associated with the resource network will contact the user.

In another embodiment, and in combination with any of the previous embodiments, the executable instructions further cause the at least one processing device to: determine a location associated with the user; determine that the location associated with the user is proximate to a resource location associated with the resource network; and transmit, to the resource location associated with the resource network that indicates, a notification that indicates that the user associated with the resource application desires assistance from personnel located at the resource location.

In another embodiment, and in combination with any of the previous embodiments, the executable instructions further cause the at least one processing device to: determine two or more resource accounts associated with the user; transmit a notification to the networked device that indicates a preferred resource account of the two or more resource accounts associated with the user to utilize for the resource transfer, receive a fifth brain activity signal that indicates a preferred resource account of the two or more resource accounts associated with the user; and process the resource transaction based the preferred resource account of the user.

In another embodiment, and in combination with any of the previous embodiments, the executable instructions that cause the at least one processing device to execute, based on receiving the third brain activity signal that indicates the determined resource transaction is the resource transaction that the user desires to complete, the resource transaction, further cause the at least one processing device to: determine that the determined resource transaction is not the resource transaction that the user desires to complete; transmit a notification that indicates a different resource transaction; receive a fifth brain activity signal that indicates that the different resource transaction is the resource transaction that the user desires to complete; and execute the different resource transaction.

In another aspect, the present disclosure is directed to a system for system for wireless communication between a brain activity monitoring system and a resource distribution device, the system comprising: at least one memory device; at least one communication device connected to a communications network; at least one processing device operatively coupled to the at least one memory device; and a module stored in the at least one memory device comprising executable instructions. The executable instructions, that when executed by the at least one processing device, cause the at least one processing device to: receive, based on a first brain activity signal from a brain activity measuring device associated with a user, a transmission that indicates a resource account and a password; determine, based on the first brain activity signal, that the password is associated with the resource account; determine, based on a second brain activity signal, a resource transaction associated with the resource account that the user desires to complete; determine an available resource distribution device associated with a resource network that can to complete the determined resource transaction that the user desires to complete; transmit, to a networked device associated with the user, a confirmation that the determined resource transaction is accurate and an indication of the available resource distribution device; process, based on a third brain activity signal that indicates the user confirmed the determined resource transaction is accurate, the determined resource transaction; and execute the determined resource transaction based on receiving an indication that the user is proximate to the available resource distribution device.

In another embodiment, and in combination with any of the previous embodiments, the executable instructions that cause the at least one processing device to execute the determined resource transaction further cause the at least one processing device to: determine one or more pending resource transactions associated with the available resource distribution device; determine, based on the one or more pending resource transactions, an estimated completion time for the available resource distribution device to execute the determined resource transaction; and transmit the estimated completion time to the networked device.

In another embodiment, and in combination with any of the previous embodiments, the executable instructions that cause the at least one processing device to execute the determined resource transaction further cause the at least one processing device to: receive, via the resource network, a notification that indicates the user is proximate to the available resource distribution device; transmit, based on the notification, a transmission to the networked device that requests the user confirm that the user is proximate the available resource distribution device and ready to execute the resource transaction; and execute, based on receiving the confirmation from the user, the resource transaction.

In another embodiment, and in combination with any of the previous embodiments, the executable instructions that cause the at least one processing device to execute the determined resource transaction further cause the at least one processing device to: receive, from the networked device via a wireless communications channel, a notification that indicates the user is proximate to the available resource distribution device; transmit, based on the notification, a transmission to the networked device that requests the user confirm that the user is proximate the available resource distribution device and ready to execute the resource transaction; and execute, based on receiving the confirmation via the wireless communications channel, the resource transaction.

In another embodiment, and in combination with any of the previous embodiments, the executable instructions that cause the at least one processing device to determine the available resource distribution device associated with the resource network further cause the at least one processing device to: determine a plurality of available resource distribution devices, wherein the plurality of available resource distribution devices comprises the available resource distribution device; determine a location associated with the user; determine, based on the location associated with the user, that the available resource distribution device is a closest resource distribution device to the user; and transmit a notification that indicates a location of the available resource distribution device.

In another embodiment, and in combination with any of the previous embodiments, the executable instructions that cause the at least one processing device to determine the available resource distribution device associated with the resource network further cause the at least one processing device to: determine a plurality of available resource distribution devices, wherein the plurality of available resource distribution devices comprises the available resource distribution device; determine a location associated with the user; determine, based on the location associated with the user, a closest resource distribution device to the user; transmit a notification that indicates the closest resource distribution device to the user; receive a fourth brain activity signal that indicates that the user is unable to access the closest resource distribution device; determine an alternative resource distribution device; and transmit a notification that indicates a location of the alternative resource distribution device.

In another embodiment, and in combination with any of the previous embodiments, the brain activity measuring device is configured to communicate with the at least one processing device via the networked device associated with the user, and wherein the brain activity measuring device is configured to measure electroencephalogram (EEG) signals associated with the user.

In another aspect, the present disclosure is directed to a system for calibration of a brain activity measuring device for detection of specific brainwave patterns, the system comprising: at least one memory device; at least one communication device connected to a communications network; at least one processing device operatively coupled to the at least one memory device; and a module stored in the at least one memory device comprising executable instructions. The executable instructions, that when executed by the at least one processing device, cause the at least one processing device to: receive from a networked device a transmission that indicates a user desires to calibrate a brain activity measuring device for accessing a resource account; receive descriptive information associated with the user that indicates a calibration procedure appropriate for the user; transmit to the networked device instructions for a first step in the calibration procedure for the user to execute; receive, based on the first step in the calibration procedure, a first brain activity signal associated with the user; modify, based on the first brain activity signal, one or more settings associated with the brain activity measuring device to improve determining brain activity signals associated with the user; transmit to the networked device a second step in the calibration procedure based on the one or more modified settings to verify the modification improved determining brain activity signals associated with the user; and store, based on receiving a second brain activity signal associated with the second step in the calibration procedure that verify the one or more modified settings improved determining brain activity signals associated with the user, the one or more modified settings.

In another embodiment, and in combination with any of the previous embodiments, the executable instructions further cause the at least one processing device to: determine, based on the descriptive information, a potential calibration procedure from a plurality of potential calibration procedures; determine, based on the first brain activity signal, that the potential calibration procedure is not appropriate for the user; and determine, based on the descriptive information and the potential calibration procedure, the calibration procedure for the user to execute.

In another embodiment, and in combination with any of the previous embodiments, the first step in the calibration procedure comprises instructing the user to concentrate on imaging a typical resource transaction associated with a resource account, and wherein the second step in the calibration procedure comprises instructing the user to concentrate on a thought that can produce a similar brain activity signal as the typical resource transaction associated with the resource account, wherein the thought is irrelevant to the typical resource transaction.

In another embodiment, and in combination with any of the previous embodiments, modifying the one or more settings associated with the brain activity measuring device further comprises: configuring the brain activity measuring device to identify the first brain activity signal as indicating the typical resource transaction associated with the resource account; and configuring the brain activity measuring device to identify the second brain activity signal as indicating an irrelevant thought that should be ignored.

In another embodiment, and in combination with any of the previous embodiments, modifying the one or more settings associated with the brain activity measuring device further comprises: configuring the brain activity measuring device to identify the first brain activity signal as indicating the typical resource transaction associated with the resource account; and configuring the brain activity measuring device to identify the second brain activity signal as indicating the typical resource transaction associated with the resource account.

In another embodiment, and in combination with any of the previous embodiments, the executable instructions further cause the at least one processing device to receive a password associated with the resource account, wherein the first step in the calibration procedure comprises instructing the user to concentrate on the password associated with the resource account, and wherein the second step in the calibration procedure comprises instructing the user to concentrate on a thought that can produce a similar brain activity signal as the password associated with the resource account.

In another embodiment, and in combination with any of the previous embodiments, modifying the one or more settings associated with the brain activity measuring device further comprises: configuring the brain activity measuring device to identify the first brain activity signal as indicating the password associated with the resource account; and configuring the brain activity measuring device to identify the second brain activity signal as indicating the password associated with the resource account.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
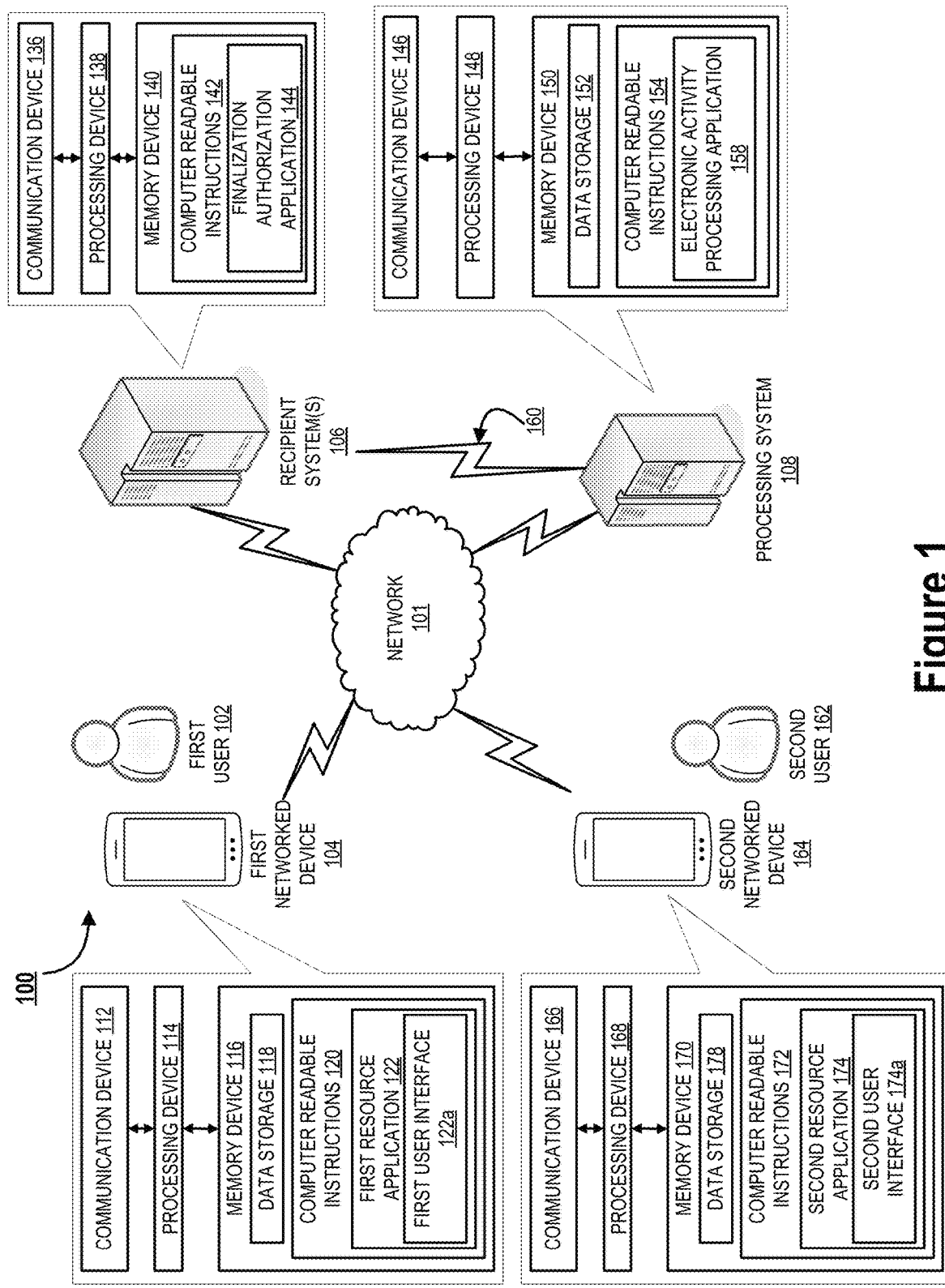
Figure 2:
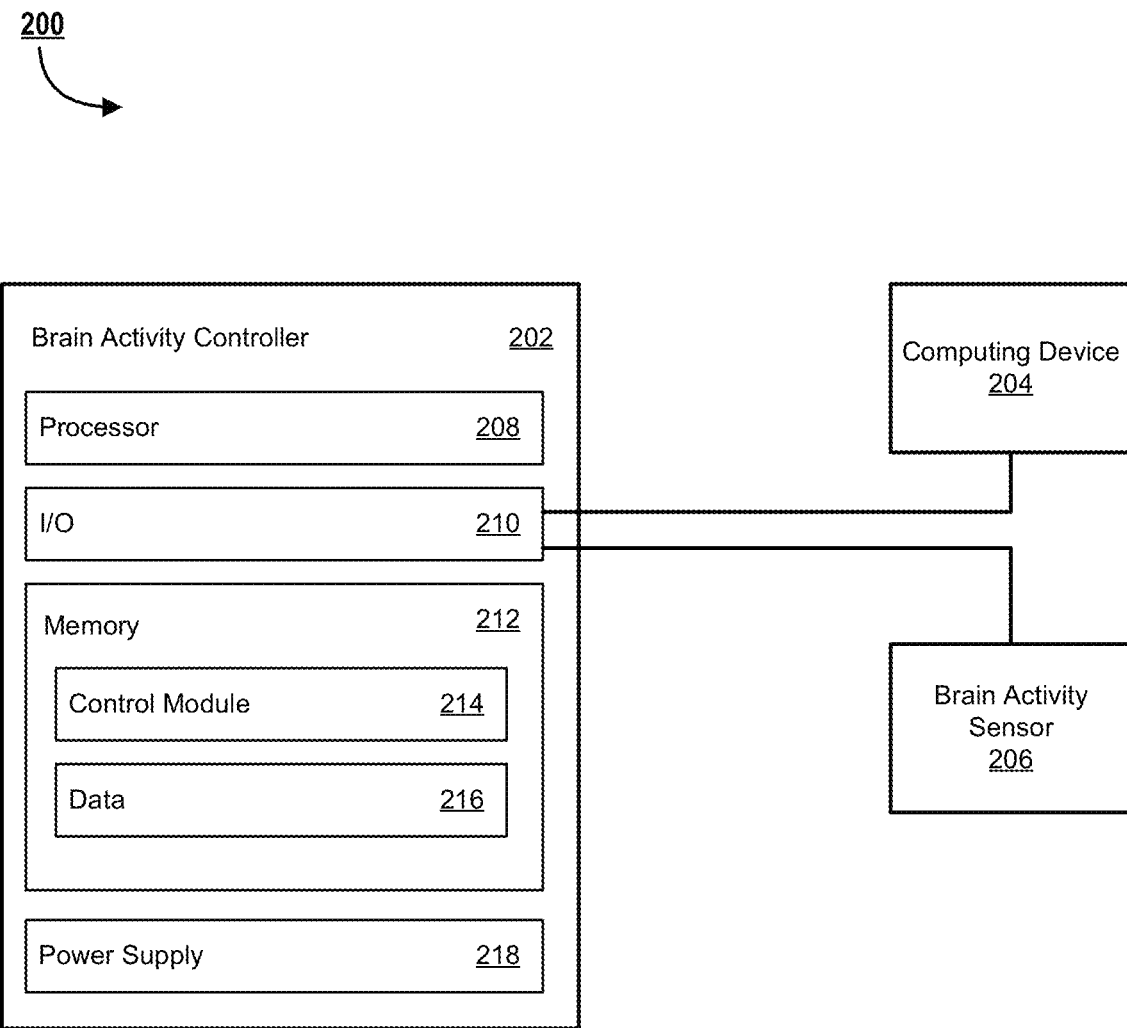
Figure 3:
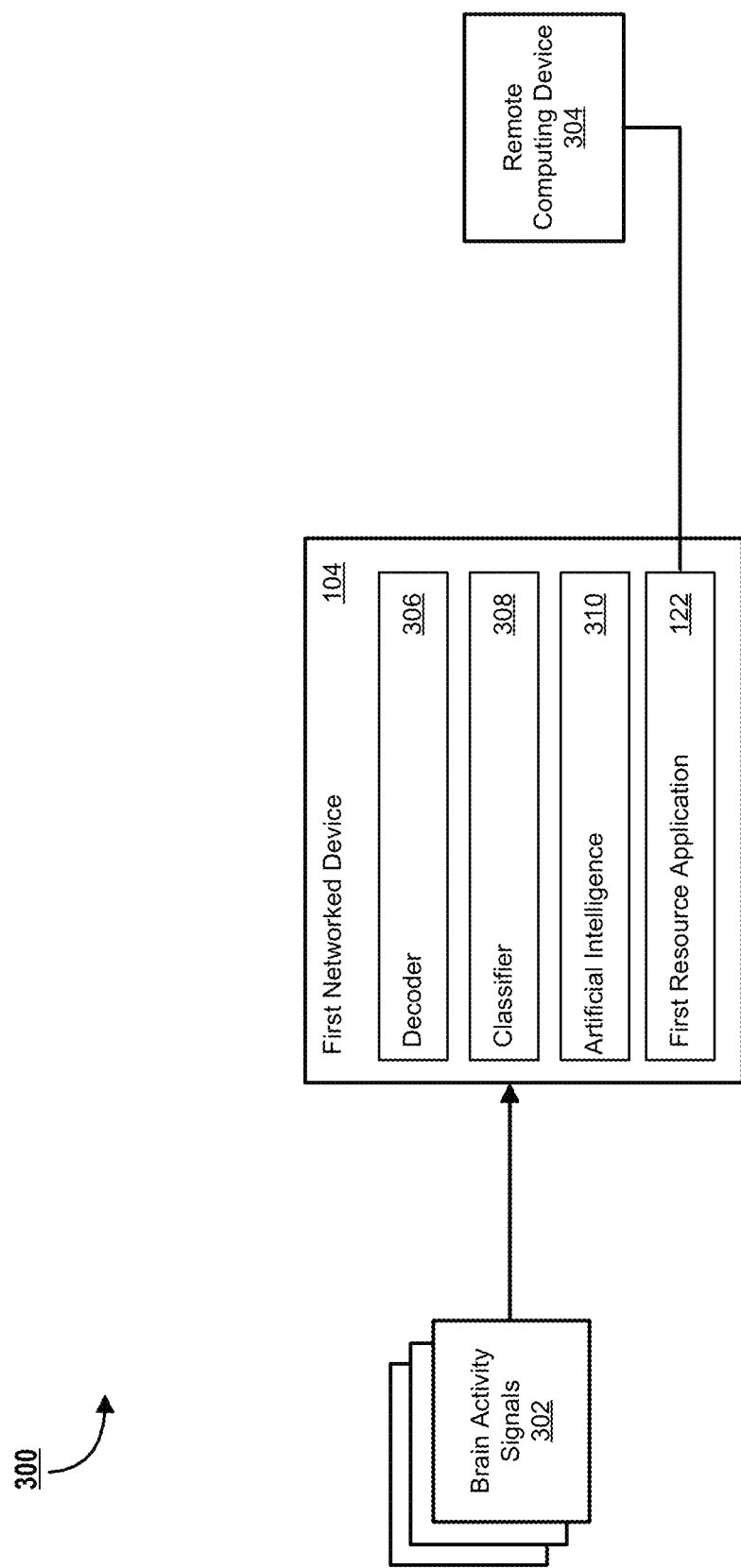
Figure 4:
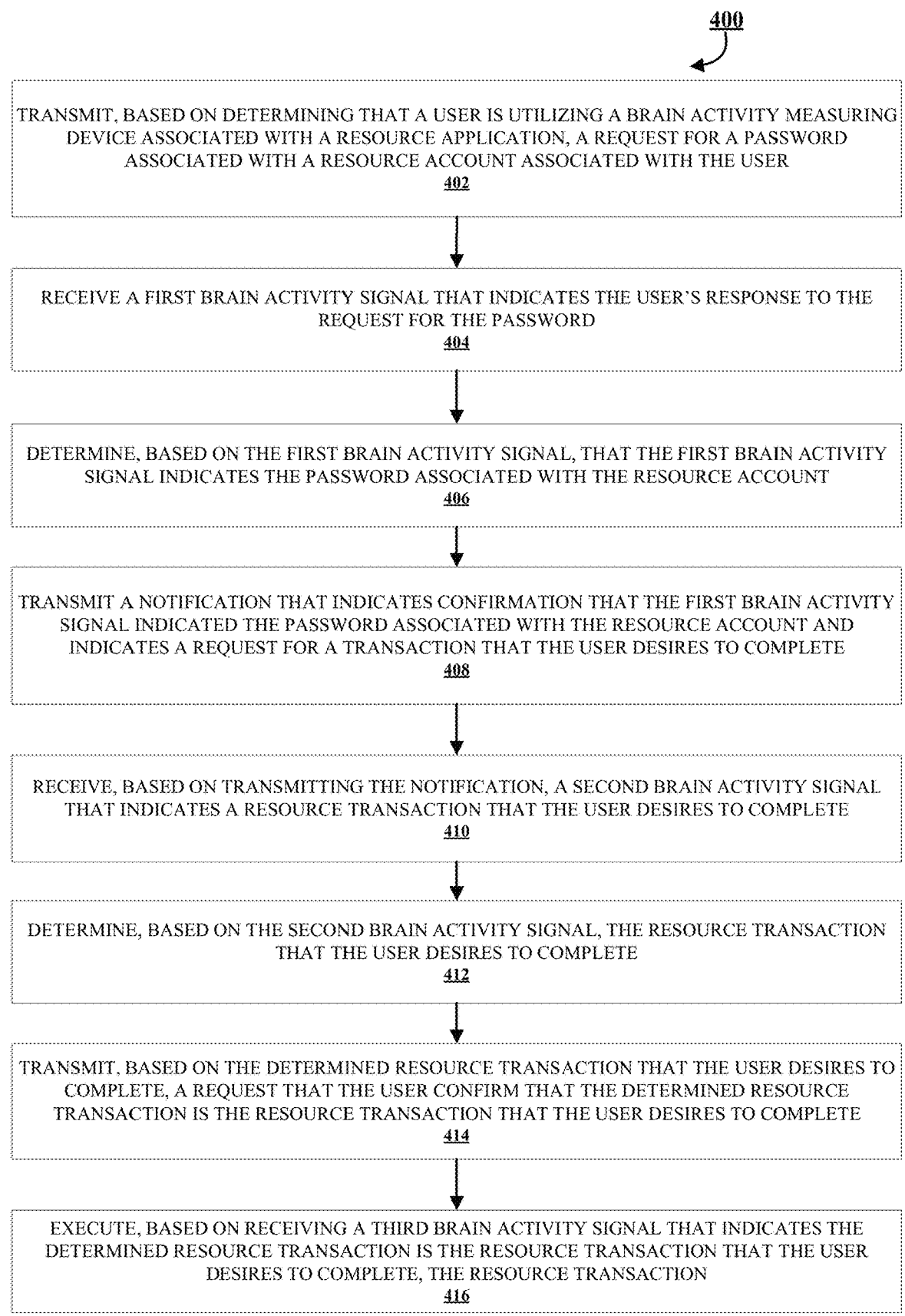
Figure 5:
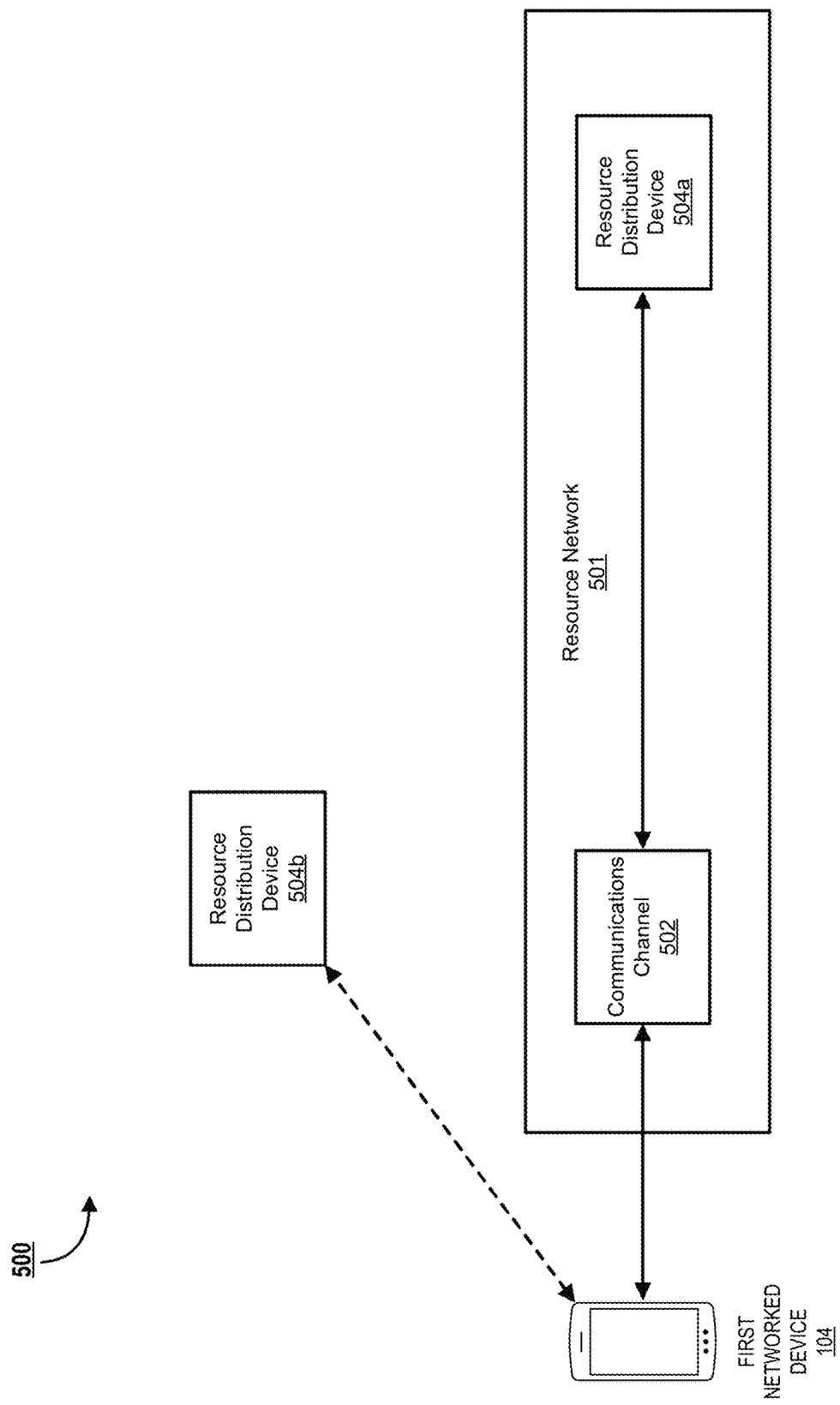
Figure 6:
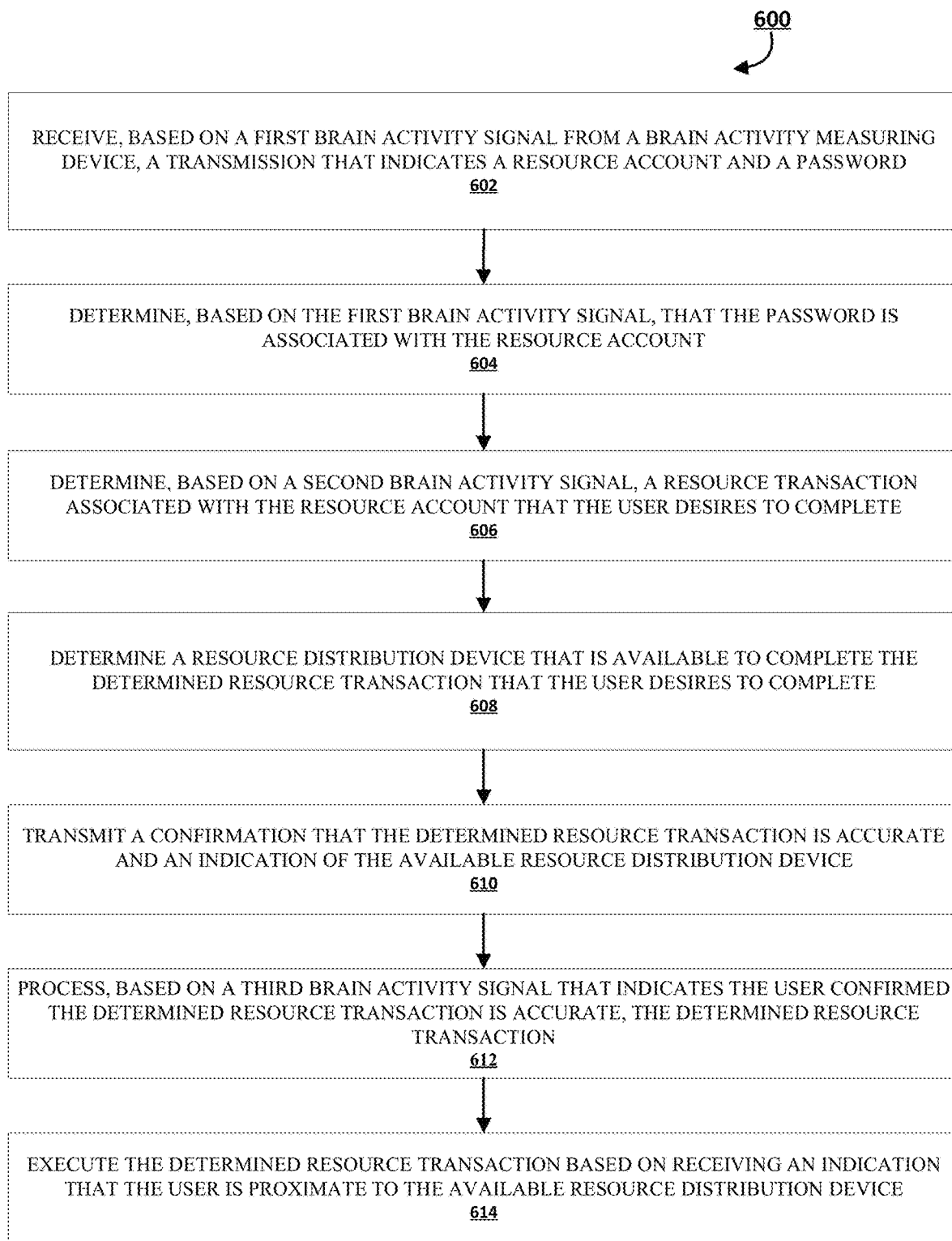
Figure 7:
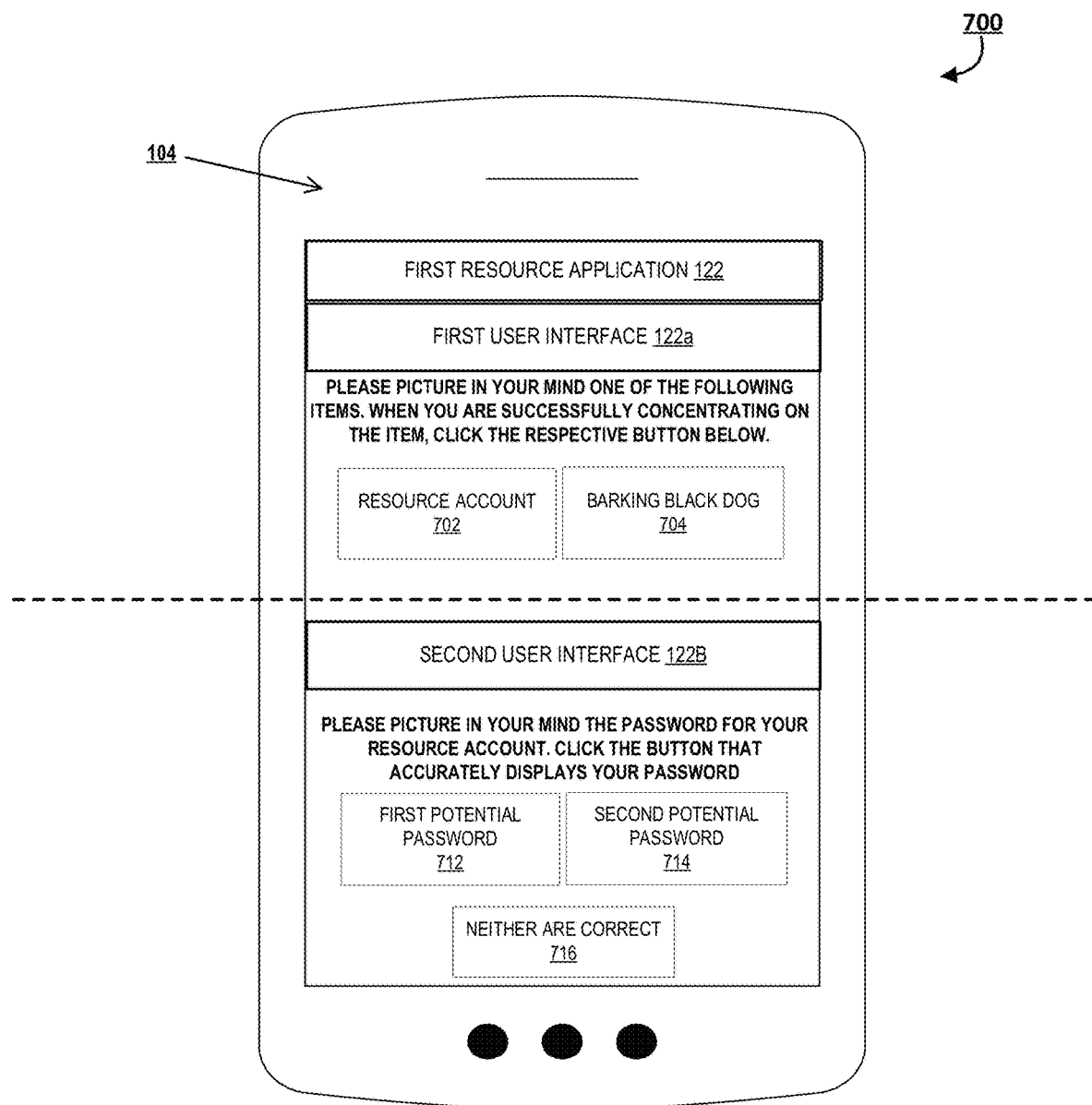

Having thus described embodiments of the invention in general terms, reference will now be made the accompanying drawings, wherein:

FIG. 1 illustrates an electronic activity processing system and environment;

FIG. 2 illustrates an exemplary brain activity monitoring system;

FIG. 3 illustrates an exemplary brain activity monitoring system;

FIG. 4 illustrates a flowchart of an exemplary method;

FIG. 5 illustrates an exemplary system for communicating with a resource distributing device;

FIG. 6 illustrates a flowchart of an exemplary method;

FIG. 7 illustrates an exemplary user interface of a device; and

Figure 8:
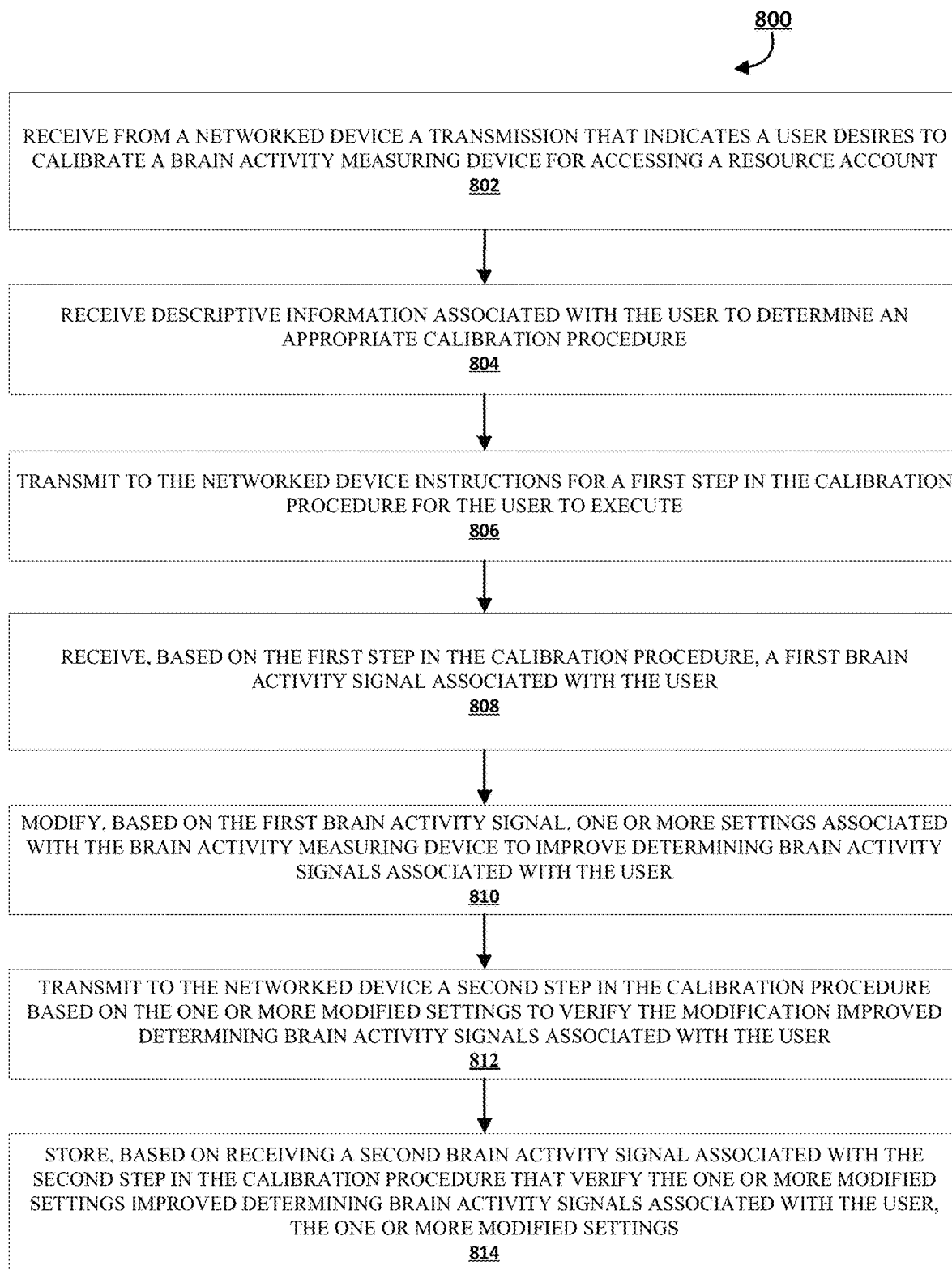

FIG. 8 illustrates a flowchart of an exemplary method.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout.

In some embodiments, an "entity" refers to an organization, a company, a group, an institute, a business or the like associated with initiating and/or performing electronic activities. Typically, the entity comprises systems, devices, applications and/or the like for initiating and/or performing electronic activities. In some embodiments, the entity initiates and/or performs electronic activities in response to receiving instructions from an associated user. In some embodiments, an "entity" as used herein may be a financial institution. For the purposes of this invention, a "financial institution" may be defined as any organization, entity, or the like in the business of moving, investing, or lending money, dealing in financial instruments, or providing financial services. This may include commercial banks, thrifts, federal and state savings banks, savings and loan associations, credit unions, investment companies, insurance companies and the like. In some embodiments, the entity may allow a user to establish an account with the entity. An "account" may be the relationship that the user has with the entity. Examples of accounts include a deposit account, such as a transactional account (e.g., a banking account), a savings account, an investment account, a money market account, a time deposit, a demand deposit, a pre-paid account, a credit account, a non-monetary user account that includes only personal information associated with the user, or the like. The account is associated with and/or maintained by an entity. In other embodiments, an "entity" may not be a financial institution. Examples for non-financial entities include cloud computing systems, database systems, block chain systems for data processing, and the like.

Unless specifically limited by the context, an "electronic activity", "user activity", "transaction" or "activity" refers to activities associated with electronic resources, such as the user's resources. In some embodiments, the electronic activity refers to resource transfers between resources, e.g., a transfer of a resource value from a first resource and a second resource. For example, the electronic activity may refer to transmission of resource value comprising predetermined data (e.g. files, text, images, and the like) from a first resource (e.g., a user device, a database, a server, a cloud storage system, and the like) to a second resource (e.g., another device, database, and the like). Typically, a first system (e.g., a user device or a networked device), for example, based on receiving instructions from a user, transmits activity parameters (e.g., location of the file, time of transmission, unique identifier of the source resource system, certificates of the target resource system, authentication information, and the like) to a recipient system (e.g., a system associated with one or more of the resources, an entity system, and the like) which then performs the electronic activity (transfer of the file from the source resource system to the target resource system). As another example, in some embodiments, the electronic activity refers to transfer of a resource value comprising financial resources (e.g. a predetermined transfer amount) from a first resource (e.g., a source user account) to a second resource (e.g., another target account). Typically, a first system (e.g., a user device), for example, based on receiving instructions from a user, transmits activity parameters (e.g., the transfer amount, time and date of the transfer, unique identifiers of the source user account and the target user account, and the like) to a recipient system (e.g., a financial institution associated with the source account and/or the target account) which then performs the electronic activity (transfer of the predetermined amount from the source user account to the target account).

As such, in some embodiments, an electronic activity or a user activity may refer to a purchase of goods or services, a return of goods or services, a payment transaction, a credit transaction, or other interaction involving a user's resources (e.g., a bank account). As another example, in some embodiments, a user activity may refer to viewing account balances, modifying user information and contact information associated with an account, modifying alert/notification preferences, viewing transaction/activity history, transferring/redeeming loyalty points and the like. In some embodiments, the user activity is associated with an entity application stored on a user device, for example, a digital wallet application, a mobile/online banking application, a merchant application, a browser application, a social media application and the like. Typically, a user activity is an electronic transaction or electronic activity in which the user is employing a mobile device, computing device, or other electronic device to initiate, execute and/or complete the activity.

As used herein, a "bank account" refers to a credit account, a debit/deposit account, or the like. Although the phrase "bank account" includes the term "bank," the account need not be maintained by a bank and may, instead, be maintained by other financial institutions. For example, in the context of a financial institution, a user activity or transaction may refer to one or more of a sale of goods and/or services, an account balance inquiry, a rewards transfer, an account money transfer, opening a bank application on a user's computer or mobile device, a user accessing their e-wallet (e.g., mobile wallet) or online banking account or any other interaction involving the user and/or the user's device that is detectable by the financial institution. As further examples, a user activity may occur when an entity associated with the user is alerted via the transaction of the user's location. A user activity may occur when a user accesses a building, uses a rewards card, and/or performs an account balance query. A user activity may occur as a user's device establishes a wireless connection, such as a Wi-Fi connection, with a point-of-sale terminal. In some embodiments, a user activity may include one or more of the following: purchasing, renting, selling, and/or leasing goods and/or services (e.g., groceries, stamps, tickets, DVDs, vending machine items, and the like); withdrawing cash; making payments (e.g., paying monthly bills; paying federal, state, and/or local taxes; and the like); sending remittances; transferring balances from one account to another account; loading money onto stored value cards (SVCs) and/or prepaid cards; donating to charities; and/or the like.

As used herein, an "online banking account" is an account that is associated with one or more user accounts at a financial institution. For example, the user may have an online banking account that is associated with the user's checking account, savings account, investment account, and/or credit account at a particular financial institution. Authentication credentials comprising a username and password are typically associated with the online banking account and can be used by the user to gain access to the online banking account. The online banking account may be accessed by the user over a network (e.g., the Internet) via a computer device, such as a personal computer, laptop, or mobile device (e.g., a smartphone or tablet). The online banking account may be accessed by the user via a mobile or online banking website or via a mobile or online banking application. A customer may access an online banking account to view account balances, view transaction history, view statements, transfer funds, and pay bills. More than one user may have access to the same online banking account. In this regard, each user may have a different username and password. Accordingly, one or more users may have a sub-account associated with the online banking account.

A "user" may be an individual or group of individuals associated with an entity that provides the system for assessing network authentication requirements based on situational instance. In some embodiments, the "user" may be a financial institution user (e.g., an account holder or a person who has an account (e.g., banking account, credit account, or the like)). In one aspect, a user may be any financial institution user seeking to perform user activities associated with the financial institution or any other affiliate entities associated with the financial institution. In some embodiments, the user may be an individual who may be interested in opening an account with the financial institution. In some other embodiments, a user may be any individual who may be interested in the authentication features offered by the financial institution/entity. In some embodiments, a "user" may be a financial institution employee (e.g., an underwriter, a project manager, an IT specialist, a manager, an administrator, an internal operations analyst, bank teller or the like) capable of operating the system described herein. For purposes of this invention, the term "user" and "customer" may be used interchangeably.

With advancements in technology infrastructures and wireless communication implementation, electronic devices such as transaction terminals such as point of sale terminals, portable multi-function devices, such as laptop computers, tablet computers, mobile phones, smart phones, wearable devices and the like are common. Typically, individuals may also have a mobile user device with them. These electronic devices may enable performance of user activities (e.g., financial activities, purchases, resource transfers, accessing resource data stored at other systems and databases and the like) based on requisite authorization. These electronic devices may also be configured to allow the user to perform the one or more user activities, transactions or resource transfers through an application, accept authentication credentials from the user, transmit authentication credentials for validation at external systems, etc.

Embodiments of the present invention address the above needs and/or achieve other advantages by providing apparatuses (e.g., a system, computer program product and/or other devices) and methods for dynamically appending and transforming static activity data transmitted to a user device application, as will be described in detail elsewhere in the specification. FIG. 1 illustrates an electronic activity processing system environment 100, in accordance with some embodiments of the present invention. FIG. 1 provides a unique system that includes specialized servers and systems, communicably linked across a distributive network of nodes required to perform the functions of processing resource transfer activities.

As illustrated in FIG. 1, a processing system 108, or electronic activity processing system 108 or application server (e.g., a financial institution system 108) is operatively coupled, via a network 101 to user devices such as a first networked device 104, a second networked device 164, etc., to the recipient system 106 (e.g., another second financial institution system 106) and/or to one or more secondary systems. In this way, the processing system 108 can send information to and receive information from the user devices such as a first networked device 104, a second networked device 164, etc., the recipient system 106, and one or more secondary systems. FIG. 1 illustrates only one example of an embodiment of the system environment 100, and it will be appreciated that in other embodiments of the systems, devices, or servers may be combined into a single system, device, or server, or be made up of multiple systems, devices, or servers.

The network 101 may be a system specific distributive network receiving and distributing specific network feeds and identifying specific network associated triggers. The network 101 may also be a global area network (GAN), such as the Internet, a wide area network (WAN), a local area network (LAN), or any other type of network or combination of networks. The network 101 may provide for wireline, wireless, or a combination wireline and wireless communication between devices on the network 101. In some embodiments, the network 101 may enable communication between devices thorough near-field communication, transmission of electromagnetic waves, sound waves or any other suitable means.

In some embodiments, the first user 102 is an individual that has a user device, i.e., the first networked device 104, such as a mobile phone, tablet, computing device, or the like and who seeks to perform one or more electronic activities or user activities. In some embodiments, the second user 162 is another individual that has a user device, i.e., the second networked device 164, such as a mobile phone, tablet, computing device, or the like and who seeks to perform one or more electronic activities or user activities.

FIG. 1 also illustrates the first networked device 104. The first networked device 104 (also referred to as a first user device or a user device, which may be associated with the first user 102) may refer to a device or a combination of devices that are configured to capture (e.g., receive and/or process) one or more instructions, inputs, authentication credentials, and the like from the user 102 such as a computing device (e.g., a mobile device, a smart phone, a laptop computer and/or another computing device), smart devices (e.g., smart TVs, smart doors, smart speakers, personal digital assistant devices), wearable devices (e.g., smart watches, fitness devices, virtual/augmented reality devices), Global Positioning System (GPS) devices, proximity/location sensors/beacon devices, visual capture devices and/or the like to capture authentication credentials associated with the user. The first networked device 104 may be, for example, a desktop personal computer, a mobile system, such as a cellular phone, smart phone, personal data assistant (PDA), laptop, or the like.

The first networked device 104 comprises a communication device 112 comprising input/output devices and/or sensors, a processing device 114, and a memory device 116. The memory device 116 can be a non-transitory computer-readable storage medium. The first networked device 104 may comprise other devices that are not illustrated, configured for location determination/navigation (GPS devices, accelerometers, etc.), for authentication (fingerprint scanners, microphones, iris scanners, etc.), for image capture (cameras, AR devices, etc.), for display (screens, touchscreens, hologram projectors, etc.), and other purposes. The first networked device 104 is a computing system that enables the user to perform one or more user activities, e.g., initiating one or more electronic activities such as resource transfers, payment requests, etc. via one or more applications associated with the first networked device 104.

The processing device 114 is operatively coupled to the communication device 112 and the memory device 116. The processing device 114 utilizes the communication device 112 to communicate with the network 101 and other devices on the network 101, such as, but not limited to, the processing system 108. For example, the communication device 112 can comprise a modem, a communications interface, a server, or other device for communicating with other devices on the network 101.

The first networked device 104 comprises the memory device 116, which can comprise computer-readable instructions 120 and data storage 118, which in one embodiment includes the computer-readable instructions 120 of a first resource application 122. The computer-readable instructions 120 can be computer-executable instructions that are executable by a processor and/or a processing device (e.g., the processing device 114). In some embodiments the first networked device 104 may refer to multiple user devices that may be configured to communicate with each other, with the processing system, and/or other systems via the network 101. In some embodiments, the processing system 108 transmits data associated with the application 122 to and/or causes the processing device 114 to install/store the first resource application 122 on the first networked device 104. In some embodiments, the first resource application 122, when executed by the processing device 114, is configured to cause the first networked device 104 to perform one or more actions and/or steps described herein. In some embodiments, the first resource application 122 is similar to the electronic activity processing application 158 described below.

The first resource application 122 may be a standalone application configured for receiving data/instructions associated with an electronic activity from a user (e.g., via the first user interface 122a of the first resource application 122), transmitting electronic data and/or executing an action associated with the resource network as described herein, or the first resource application 122 may refer to one or more existing applications on the user device that are configured to perform one or more of these steps. In some embodiments, the first resource application 122 may be associated with a resource network application that facilitates the first user 102 interacting with a resource network. For example, the first resource application 122 may be a payment network application structured for person-to person (P2P) payments and/or real time payments (RTP), with the second user 162 being a part of the same payment network and having a corresponding payment network application structured for person-to person (P2P) payments and/or real time payments (RTP) (second resource application 174). In some embodiments, the resource network may comprise the processing system 108 and/or a financial institution system may transmit electronic communications to the first networked device 104, which may be configured to cause the first resource application 122 to perform one or more functions, actions, or steps associated with electronic processing. For example, the electronic communications may cause the first resource application 122 to trigger one or more sensors or input devices of the first networked device 104 to capture and/or receive an authentication credential associated with the first user 102 based on instructions received via the electronic communications. The electronic communications may originate from the processing system 108, or another computing device in the system 100, to cause the first networked device 104 to request user input/information from the first user 102, and the like.

FIG. 1 also illustrates the second networked device 164. The second networked device 164 (also referred to as a second user device or a user device, which may be associated with the second user 162) may refer to a device or a combination of devices that are configured to capture (e.g., receive and/or process) one or more instructions, inputs, authentication credentials, and the like from the second user 162 such as a computing device (e.g., a mobile device, a smart phone, a laptop computer and/or another computing device), smart devices (e.g., smart TVs, smart doors, smart speakers, personal digital assistant devices), wearable devices (e.g., smart watches, fitness devices, virtual/augmented reality devices), GPS devices, proximity/location sensors/beacon devices, visual capture devices and/or the like to capture authentication credentials associated with the user. The second networked device 164 may be, for example, a desktop personal computer, a mobile system, such as a cellular phone, smart phone, personal data assistant (PDA), laptop, or the like.

The second networked device 164 comprises a communication device 162 comprising input/output devices and/or sensors, a processing device 168, and a memory device 170. The memory device 170 can be a non-transitory computer-readable storage medium. The second networked device 164 may comprise other devices that are not illustrated, configured for location determination/navigation (GPS devices, accelerometers, etc.), for authentication (fingerprint scanners, microphones, iris scanners, etc.), for image capture (cameras, AR devices, etc.), for display (screens, touchscreens, hologram projectors, etc.), and other purposes. The second networked device 164 is a computing system that enables the user to perform one or more user activities, e.g., initiating one or more electronic activities such as resource transfers, payment requests, etc. via one or more applications associated with the first networked device 104.

The processing device 168 is operatively coupled to the communication device 162 and the memory device 170. The processing device 168 utilizes the communication device 162 to communicate with the network 101 and other devices on the network 101, such as, but not limited to the processing system 108. For example, the communication device 162 can comprise a modem, a communications interface, a server, or other device for communicating with other devices on the network 101.

The second networked device 164 comprises the memory device 170, which can comprise computer-readable instructions 172 and data storage 178, which in one embodiment includes the computer-readable instructions 172 of a second resource application 174. The computer-readable instructions 172 can be computer-executable instructions that are executable by a processor and/or a processing device (e.g., the processing device 168). In some embodiments, the second networked device 164 may refer to multiple user devices that may be configured to communicate with each other, with the processing system, and/or other systems via the network 101. In some embodiments, the processing system 108 transmits data associated with the application 174 to and/or causes the processing device 168 to install/store the second resource application 174 on the second networked device 164. In some embodiments, the second resource application 174, when executed by the processing device 168, is configured to cause the second networked device 164 to perform one or more actions and/or steps described herein. In some embodiments, the second resource application 174 is similar to the electronic activity processing application 158 described below.

The second resource application 174 may be a standalone application configured for receiving data/instructions associated with an electronic activity from a user (e.g., via the second user interface 174a of the second resource application 174), transmitting electronic data and/or executing an action associated with the resource network as described herein, or the second resource application 174 may refer to one or more existing applications on the user device that are configured to perform one or more of these steps. In some embodiments, the second resource application 174 associated with the second user 162 may be associated with a resource network. For example, the second resource application 174 may be a payment network application structured for person-to person (P2P) payments and/or real time payments (RTP), with the first user 102 being a part of the same payment network and having a corresponding payment network application structured for person-to person (P2P) payments and/or real time payments (RTP) (first resource application 122). In some embodiments, the processing system 108 and/or a financial institution system may transmit electronic communications to the second networked device, which may be configured to cause the second resource application 174 to perform one or more functions or steps associated with electronic processing. For example, the electronic communications may cause the second resource application 174 to trigger one or more sensors or input devices of the second networked device 164 to capture and/or receive an authentication credential associated with the second user 162 based on instructions received via the electronic communications. The electronic communications may originate from the processing system 108, or another computing device in the system 100, to cause the second networked device 164 to request user input/information from the second user 162, and the like.

As further illustrated in FIG. 1, the processing system 108 or the electronic activity processing system 108 generally comprises a communication device 146, a processing device 148, and a memory device 150. The memory device 150 can be a non-transitory computer-readable storage medium. As used herein, the term "processing device" generally includes circuitry used for implementing the communication and/or logic functions of the particular system. For example, a processing device may include a central processing unit (CPU), a digital signal processor device, a microprocessor device, and various analog-to-digital converters, digital-to-analog converters, and other support circuits and/or combinations of processing devices. Control and signal processing functions of the system are allocated between these processing devices according to their respective capabilities. The processing device 108 may be configured to operate one or more software programs and/or applications based on computer-readable instructions 154, which may be stored in a memory device 150. The computer-readable instructions 154 can be computer-executable instructions that are executable by a processor and/or a processing device (e.g., the processing device 148).

The processing device 148 is operatively coupled to the communication device 146 and the memory device 150. The communication device 146 can comprise a modem, a server, a communications interface, or other device for communicating with other devices on the network 101. The processing device 148 uses the communication device 146 to communicate with the network 101 and other devices on the network 101, such as, but not limited to the recipient system 106, the user device(s) 104, 164, and/or additional devise in communication with the network 101.

The processing system 108 comprises computer-readable instructions 154 stored in the memory device 150, which in one embodiment includes the computer-readable instructions 154 of an electronic activity processing application 158. In some embodiments, the memory device 150 includes data storage 152 for storing data associated with the processing system 108. For example, the data can be associated with the electronic activity processing application 158, the system 108, and/or the system 100. In some embodiments, executing the computer readable instructions of the electronic activity processing application 158 causes the processing device 148 to perform one or more steps and/or actions for electronic activity processing described herein.

The electronic activity processing application 158 may receive electronic activity data from the user devices, e.g., the first networked device 104 and/or the second networked device 164. In some embodiments, the processing system 108 may retrieve user authentication information, capture device information, financial information, identifiers, resource account information, and the like from the user devices (e.g., the first networked device 104, the second networked device 164, etc.) and/or the recipient system 106. In this way, the electronic activity processing application 158 may communicate with the recipient system 106, the user devices (e.g., the first networked device 104, the second networked device 164, etc.), a resource network, merchant systems, and other third-party systems.

In some embodiments, the electronic activity processing application 158 may control the functioning of the first networked device 104 and/or the second networked device 164. In some embodiments, the electronic activity processing application 158 may comprise computer readable instructions 154 or computer-readable program code, that when executed by the processing device 148, causes the processing device 148 to perform one or more steps described herein and/or transmit data to other systems and devices to cause the systems and devices to perform specific tasks. For example, the electronic activity processing application 158 may initiate a transfer of resources from a first resource to a second resource.

As illustrated in FIG. 1, the recipient system 106 is connected to the processing system 108 and may be associated with a financial institution network (e.g., a recipient bank for a resource transfer activity, an account transfer electronic activity, etc.). The recipient system 106 may refer to a financial institution system, a transaction terminal or other devices or systems associated with performing the activity. In this way, while only one recipient system 106 is illustrated in FIG. 1, it is understood that multiple network systems may make up the system environment 100. In some embodiments, the recipient system 106 is substantially similar to the processing system 108. The recipient system 106 generally comprises a communication device 136, a processing device 138, and a memory device 140. The memory device 140 can be a non-transitory computer-readable storage medium. The recipient system 106 comprises computer-readable instructions 142 stored in the memory device 140, which in one embodiment includes the computer-readable instructions 142 of a finalization authorization application 144. The computer-readable instructions 142 can be computer-executable instructions that are executable by a processor and/or a processing device (e.g., the processing device 138). In some embodiments, the processing system 108 (e.g., based on executing the application 158) transmits and/or causes the processing device 138 to install/store the finalization authorization application 144 on the recipient system 106. In some embodiments, the finalization authorization application 144, when executed by the processing device 138 is configured to cause the recipient system 106 to perform one or more steps described herein (e.g., transfer resources from a first resource to a second resource). In some embodiments, the finalization authorization application 144 is similar to the electronic activity processing application 158 described above. The recipient system 106 may communicate with the processing system 108 to receive static activity data sets, indicate processing of static activity data sets, indicate completion of an electronic activity, request validation of authentication credentials, confirm a resource transfer, and the like. The processing system 108 may communicate with the recipient system 106 via a secure connection 160 generated for secure encrypted communications between the two systems. In some embodiments, the secure connection 160 may be an operative communication link/channel established via the network 101.

It is understood that the servers, systems, and devices described herein illustrate one embodiment of the invention. It is further understood that one or more of the servers, systems, and devices can be combined in other embodiments and still function in the same or similar way as the embodiments described herein.

FIG. 2 illustrates an exemplary brain activity monitoring system 200. As shown, the system 200 comprises a brain activity controller 202, a computing device 204, and a brain activity sensor 206. While the brain activity controller 202 (may be referred to simply as controller 202) and the brain activity sensor 206 (may be referred to simply as sensor 206) are illustrated as separate devices for ease of explanation, in one exemplary embodiment the controller 202 and the sensor 206 are configured on a single device. For example, an electroencephalogram (EEG) device and/or apparatus can comprise the controller 202 and the sensor 206. Further, the controller 202 apparatus can also include the computing device 204.

The controller 202 comprises a processor 208, an input output interface (I/O) 210, a memory 212, and a power supply 218. In some embodiments, the controller 202 can include additional parts such as global positioning system (GPS), motion detectors, and so forth. While a single processor 208 is shown for ease of explanation, a person skilled in the art would appreciate that the controller 202 can include any number of processors 202. Further, the controller 202 can comprise one or more microcontrollers.

The processor 208 can perform various tasks, such as retrieving information stored in the memory 212, and executing various software modules. For example, the processor 208 can execute the control module 214 that provides instructions and/or settings to the brain activity sensor 206. As an example, the control module 214 can provide instructions and/or settings for a brain activity scan and/or measurement utilizing the sensor 206. In one example, the processor 208 can be a microcontroller.

As shown, the controller 202 is communicatively coupled via the I/O 210 with the computing device 204 and the sensor 206. The I/O 210 can include any type of suitable hardware for communication with the computing device 204 and/or the brain activity sensor 206. For example, the I/O 210 can include direct connection interfaces such as Ethernet and Universal Serial Bus (USB), as well as wireless communications, including but not limited to, Wi-Fi, Bluetooth, cellular, Radio Frequency (RF), and so forth. Further, the I/O 210 can include a multiplexer for amplification, filtering, and/or digitization of signals. For example, the multiplexer can amplify, filter, and/or digitize the signals provide by the sensor 206. As an example, the multiplexer can receive the signals (e.g., the output) from the sensor 206 and can amplify the received signals.

The brain activity sensor 206 is configured to measure one or more signals related to brain activity of a user (e.g., the first user 102). For example, the sensor 206 can be an EEG device that produces signals based on brain activity detected by the sensor 206. The brain activity sensor 206 can transmit the measured signals to one or more devices (e.g., the brain activity controller 202, the computing device 204, etc.). While not shown for ease of explanation, the brain activity sensor 206 may further comprise a microcontroller that can be configured to control the brain activity sensor 206. The brain activity sensor 206 can also include additional sensors such as a motion sensor (not shown). The motion sensor can include an accelerometer, a gyroscope, a Global Positioning System (GPS) sensor, or any other sensor for detecting motion. For example, the motion sensor can detect motion of user that is coupled to the brain activity sensor 206.

The memory 212 includes a control module 214 and data 216. The memory 212 typically comprises a variety of computer readable media. As an example, computer readable media can be any available media and comprises, for example and not meant to be limiting, both volatile and non-volatile media, removable and non-removable media. The memory 206 can comprise computer readable media in the form of volatile memory, such as random access memory (RAM), and/or non-volatile memory, such as read only memory (ROM).

In another example, the memory 212 can also comprise other removable/non removable, volatile/non-volatile computer storage media. The memory 212 can provide non-volatile storage of computer code, computer readable instructions, data structures, program modules, and other data for the controller 202. For example, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

The memory 212 can store software that is executable by the processor 208, including operating systems, applications, and related software. The memory 212 also includes data 216. The data 216 can include data and/or signals received from the brain activity sensor 206, settings or preferences for the brain activity sensor 206, or any relevant type of data. As an example, the data 216 can include data and/or signals related to the output of the brain activity sensor 206. While not shown, a person skilled in the art would appreciate that the memory 212 can also include additional software and/or firmware for operating the controller 202.

The controller 202 also includes a power supply 218. The power supply 218 can be any suitable method of providing power to the controller 202 and/or the brain activity sensor 106. While not shown for ease of explanation, the computing device 204 and/or the brain activity sensor 206 can also comprise a power supply. The power supply 218 can include a battery (e.g., Lithium-Ion, alkaline, etc.), a direct power connection (e.g., wired) to an external source (e.g., 120 V, 240 V), and/or a wireless power connection (e.g., induction) to an external source. The power supply 218 can comprise one or more components configured to provide a constant voltage to the controller 202, as well as to the sensor 206. The power supply 218 can also have a stable current source to provide stable current to the controller 202, as well as to the sensor 206. In one embodiment, the power supply 218 is a battery providing power for the controller 202 to operate, as well as power to operate the sensor 206. In this manner, the controller 202 and the brain activity sensor 206 can be untethered from other electronic devices in order to a user coupled to the sensor 206 to more freely. Further, as will be appreciated by one skilled in the art, the power supply 218 can include additional elements such as amplifiers, filters, and so forth. While a single power supply 218 is illustrated for ease of explanation, a person skilled in the art would appreciate additional power supplies 218 may be present that may include similar or different power sources.

The brain activity sensor 206 can provide and/or transmit signals and/or data to the controller 202. The controller 202 can store the received data and/or signals from the brain activity sensor 206, as well as provide the received data and/or signals to the computing device 204. The controller 202 and/or the computing device 204 can utilize the data and/or signals to make one or more determinations regarding the brain activity of a user coupled to the sensor 206. The controller 202 and/or the computing device 204 can determine one or more thoughts and/or intentions of the user coupled to the sensor 206. For example, the controller 202 and/or the computing device 204 can receive signals from the sensor 206 and can determine a thought and/or intention associated with the received signals. The controller 202 and/or the computing device 204 can store data (e.g., the data 216) associated with the received signals.

In one embodiment, the control module 214 includes the capability to operate the sensor 206. For example, the control module 214 includes the capability to communicate with the sensor 206 and provide operational instructions and/or preferences to the sensor 206. The control module 214 can provide control signals to the sensor 206 to run a scan and/or measurement for brain activity. For example, the control module 214 can provide signals to the sensor 206 to activate and produce data and/or signals that indicate the brain activity of a user coupled to the sensor 206. The control module 214 can receive the data and/or signals from the brain activity sensor 206 and provide the data and/or signals to the computing device 204. For example, the computing device 204 can be associated with a resource application (e.g., the resource application 122, 174) configured to take one or more actions based on the data and/or signals. The resource application can be configured to control operation of the brain activity controller 202 and/or the brain activity sensor 206. For example, the resource application can determine that one or more settings associated with the controller 202 and/or the brain activity sensor 206 need to be modified based on the received data and/or signals. As an example, the received data and/or signals may not be clear enough (e.g., legible to the resource application) due to interference. The resource application may send a communication and/or data to the controller 202 and/or the sensor 206 to modify one or more settings to reduce the impact of the interference.

The brain activity controller 202 can be configured to calibrate the brain activity sensor 206. The controller 202 can communicate with the computing device 204 to walk a user coupled to the brain activity sensor 206 through a calibration procedure to ensure that the brain activity sensor 206 is properly measuring the user's thoughts and/or intentions. For example, the user's thoughts and/or intentions may provide data and/or signals that are similar to data and/or signals that are unrelated to the user's thoughts and/or intentions so the brain activity sensor 206 needs to be calibrated. As an example, the data and/or signals produced by the sensor 206 when the user thinks "initiate resource transfer" or "contact personnel to receive assistance" may appear similar to when a user thinks about "a black dog barking." Thus, the computing device 204 can walk the user through a calibration procedure and can communicate with the controller 202 to properly adjust one or more settings associated with the sensor 206 to more accurately determine the thoughts and/or intentions of the user coupled to the brain activity sensor 206.

The brain activity controller 202 can be configured to communicate with a resource distribution device. For example, the computing device 204 can be the resource distribution device and/or the controller 202 can communicate with the resource distribution device via the computing device 204. The controller 202 can transmit data and/or signals that indicate that the user coupled to the sensor 206 desires to take one or more actions associated with the resource distribution device. As an example, the computing device 204 may comprise a resource application that is configured to communicate with the resource distribution device. The controller 202 can transmit the data and/or signals received from the sensor 206 to the computing device 204 that indicate the user desires to take one or more actions associated with the resource distribution device. The computing device 204 may transmit data to the resource distribution device to indicate the one or more actions based on the thoughts and/or intentions of the user. The resource distribution device may execute the desired one or more actions to perform the thoughts and/or intentions of the user.

FIG. 3 illustrates an exemplary brain activity monitoring system 300. Specifically, the system 300 illustrates the first networked device 104 of FIG. 1 receiving brain activity signals 302 (e.g., from the brain activity controller 202 and/or the brain activity sensor 206 of FIG. 2) and communicating with a remote computing device 304. For example, the first networked device 104 can utilize the first resource application 122 to communicate with the remote computing device 304. The first resource application 122 may be configured to execute one or more actions associated with a resource network based on the thoughts and/or intentions of the user associated with the brain activity signals 302.

The first networked device 104 can have a decoder 306 configured to decode the brain activity signals 302. For example, the first networked device 104 can receive brain activity signals 302 that are received directly from a sensor. The decoder 306 can decode (e.g., translate) the received signals into data that is capable of being read by a computing device. As an example, the brain activity signals 302 may be electrical signals that are not usable by the first networked device 104. The decoder 306 can receive the electrical signals and convert the electrical signals into a format that is usable the first networked device. For example, the decoder 306 can convert the electrical signals to data capable of being processed by the first networked device 104.

The first networked device 104 can also have a classifier 308 for classifying the brain activity signals 302. The decoder 306 can be configured to provide the classifier 308 with the data produced from the converted electrical signals. The classifier 308 can be configured to receive the data and output a probability that indicates the accuracy of the classification of the data. For example, the classifier 308 can output that the received data has a 0.85 probability to be "withdraw a resource from a distribution device." The classifier 308 can provide the output to the first resource application 122 to facilitate completing the users desired thoughts and/or intentions. The classifier 308 may be a trained classifier that was trained from a training data set. The training data set may comprise previously known data that indicates a known input with a known result. The classifier 308 can be trained based on this training data set to more accurately determine the thoughts and/or intentions of the user. Additionally, the classifier 308 can be continually trained based on all of the data the classifier 308 receives to further refine and improve the operation of the classifier 308.

The first networked device 104 can utilize artificial intelligence 310. The artificial intelligence 310 can include machine learning or any other form of device learning. The artificial intelligence 310 can be configured to personalize a brain activity monitoring device (e.g., the brain activity controller 202, the first networked device 104, etc.). For example, the artificial intelligence 310 can personalize the brain activity monitoring device based on one or more descriptive data and/or properties of a user. As an example, each person that utilizes the brain activity monitoring device may have a baseline of neuron activity that is unique to each person, similar to a fingerprint, so that no two people have an identical baseline of neuron activity. The artificial intelligence 310 may learn a user's baseline neuron activity over time to improve identification of the user. Further, the artificial intelligence 310 can receive preferences associated with a user to modify the operation of the brain activity monitoring device based on the preferences associated with the user. For example, the user associated with the first networked device 104 can provide the artificial intelligence 310 with one or more properties and/or descriptive data associated with the user to allow the artificial intelligence 310 to further personalize the brain activity monitoring of the user. A personalized account can be generated that is associated with each user to store the descriptive information and/or properties of the user. The personalized account can be utilized to determine a proper calibration procedure, as well as improve the functioning of the brain waive monitoring device and/or the artificial intelligence 310.

The artificial intelligence 310 can be configured to determine a personalized password associated with the user. For example, the user may have a resource account that has an associated password. The artificial intelligence may utilize the brain activity signals 302 to determine whether the password provided by the user matches the password associated with the resource account. While the term "password" is used for ease of explanation, the term encompasses more than simply a password. Rather, the "password" as described herein is associated with one or more brain activity signals 302 that the artificial intelligence 310 can utilize and/or read to determine the "password" generated by the user. As an example, the artificial intelligence 310 can utilize the aforementioned baseline neuron activity, which may be unique to each person, as a password for the user. As another example, the password may be an image the user utilizes to generate one or more brain activity signals 302 based on their thoughts. For example, the password could be a visual image of a "barking black dog playing with a fluffy ball," which causes the user to generate one or more brain activity signals 302 based on the thought of the visual image. While the password could simply be the passphrase "barking black dog playing with a fluffy ball," such a definition does not properly encompass the personal aspects of the visual image that each user would generate. That is, a first person and a second person could be told to picture a visual image of a "barking black dog playing with a fluffy ball," and both users are likely to conjure two visually distinct images. For example, the first person could imagine a small five pound dog and/or puppy playing with a tiny fluffy ball, whereas the second user could image a large sixty pound dog playing with an oversized tennis ball. Accordingly, both the first person and the second person conjured an image about a "barking black dog playing with a fluffy ball," but the images are vastly different. Thus, the brain activity signals for the first person and the second person will be very different. Therefore, the password may be a one or more brain activity signals that the user intends to indicate the password. Accordingly, the artificial intelligence 310 can improve the analysis of the brain activity signals 302 (e.g., learn) based on the brain activity signals associated with each user.

The artificial intelligence 310 may be configured to implement any of the following applicable machine learning algorithms either singly or in combination: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style.

Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of machine learning algorithm.

The artificial intelligence 310 can additionally or alternatively leverage: a probabilistic module, heuristic module, deterministic module, or any other suitable module leveraging any other suitable computation method, machine learning method or combination thereof. However, any suitable machine learning approach can otherwise be incorporated in the artificial intelligence 310. Further, any suitable model (e.g., machine learning, non-machine learning, etc.) can be used in generating data relevant to the artificial intelligence 310. While the artificial intelligence 310 was described as component of the first networked device 104 for ease of explanation, the remote computing device 304 may also comprise the artificial intelligence 310, as will be appreciated by one skilled in the art. Accordingly, in an exemplary embodiment, both the remote computing device 304 and the first networked device 104 can comprise the artificial intelligence 310.

FIG. 4 illustrates a flowchart of an exemplary method 400. The method 400 can be a computerized method. At block 402, a computing device transmits, based on determining that a user is utilizing a brain activity measuring device associated with a resource application, a request for a password associated with a resource account associated with the user. For example, the computing device can receive an electronic communication and/or transmission from another computing device, such as the first networked device 104, that indicates the user is utilizing a brain activity measuring device. The brain activity measuring device can be configured to communicate with the computing device via a first networked device associated with the user. In one embodiment, the brain activity measuring device is configured to measure electroencephalogram (EEG) signals associated with the user. The computing device can transmit the request for the password in response to determine the user's desire to take one or more actions associated with the resource application. The computing device can transmit the request for the password to confirm that user is authorized to access the resource application and/or a resource account that the user is attempting to access. The password can be a password, a phrase, neuron activity of the user, an image, and so forth. For example, the password may be an image the user utilizes to generate one or more brain activity signals based on their thoughts. As an example, the password could be a visual image of a "barking black dog playing with a fluffy ball," which causes the user to generate one or more brain activity signals based on the thought of the visual image. While the password could simply be the passphrase "barking black dog playing with a fluffy ball," such a definition does not properly encompass the personal aspects of the visual image that each user would generate. That is, a first person and a second person could be told to picture a visual image of a "barking black dog playing with a fluffy ball," and both users are likely to conjure two visually distinct images. For example, the first person could imagine a small five pound dog and/or puppy playing with a tiny fluffy ball, whereas the second user could image a large sixty pound dog playing with an oversized tennis ball. Accordingly, both the first person and the second person conjured an image about a "barking black dog playing with a fluffy ball," but the images are vastly different. Thus, the brain activity signals for the first person and the second person will be very different. Therefore, the password may be a one or more brain activity signals that the user intends to indicate the password.

At block 404, the computing device receives a first brain activity signal that indicates the user's response to the request for the password. For example, the computing device can receive an electronic communication from the another computing device that indicates the user's thoughts and/or intentions associated with the password. The electronic communication may indicate a resource account associated with the user and/or the resource application.

At block 406, the computing device determines, based on the first brain activity signal, that the first brain activity signal indicates the password associated with the resource account. The resource account can be associated with a resource network. The computing device may communicate with the resource network to determine the correct password for the resource account. The computing device can compare the received password with the correct password to determine whether the password is correct.

At block 408, the computing device transmits a notification that indicates confirmation that the first brain activity signal indicated the password associated with the resource account and indicates a request for a transaction that the user desires to complete. For example, the computing device may provide a list of possible transactions associated with the resource application and/or the resource account to the another computing device.

At block 410, the computing device receives, based on transmitting the notification, a second brain activity signal that indicates a resource transaction that the user desires to complete. For example, the computing device can receive an electronic communication from the another computing device that indicates the second brain activity signal associated with the user.

At block 412, the computing device determines, based on the second brain activity signal, the resource transaction that the user desires to complete. For example, the user can have a thought and/or intention to "execute resource transfer" to indicate that the user desires to transfer a quantity of the resource from a first resource account to a second resource account. As another example, the second brain activity signal may indicate that the user desires assistance from personnel associated with a resource network.

At block 414, the computing device transmits, based on the determined resource transaction that the user desires to complete, a request that the user confirm that the determined resource transaction is the resource transaction that the user desires to complete. The computing device can transmit an electronic communication to the another computing device with an indication of the thought and/or intention that the computing device believes the user desires. For example, the computing can transmit an electronic communication that requests that the user confirm that the desire to "execute a resource transfer." The computing device may determine that the are two or more resource accounts associated with the user. The computing device can be configured to transmit a notification to the networked device that requests the user to indicate a preferred resource account of the two or more resource accounts. For example, the notification can instruct the user to select the preferred resource account to utilize for the resource transaction. The computing device can receive a brain activity signal associated with the user that indicates the resource account that the user desires to use.

At block 416, the computing device executes, based on receiving a third brain activity signal that indicates the determined resource transaction is the resource transaction that the user desires to complete, the resource transaction. For example, the computing device can receive an electronic communication from the another computing device that indicates the third brain activity signal associated with the user. The third brain activity signal can indicate that the user confirmed that the user desires to "execute a resource transfer."

In another embodiment, and in combination with any of the previous embodiments, the executable instructions further cause the at least one processing device to: receive a fourth brain activity signal associated with the user; determine that the fourth brain activity signal that is associated with brain activity that is undeterminable; transmit a notification that indicates the fourth brain activity signal is associated with brain activity that is undeterminable; and receive, in response to transmitting the notification, a fifth brain activity signal that is determinable.

In another embodiment, the computing device may determine that the resource transaction is associated with the user desiring assistance from personnel associated with a resource network. The computing device may transmit, to a device associated with the resource network, a notification that indicates that the user desires assistance from the personnel associated with the resource network. For example, the computing device may contact personnel at a branch and/or headquarters of the resource network to indicate that the user desires assistance. The computing device can also be configured to transmit to the first networked device a notification that the personnel associated with the resource network will contact the user to confirm that the user will receive assistance as requested. Additionally, the computing device can determine a location associated with the user. For example, the computing device may receive data that indicates the location of the user or may determine the location of the user via one or more devices, such as GPS. Based on the location associated with the user, the computing can determine that the user is proximate to a resource location associated with the resource network. The computing device can transmit a notification to the resource location associated with the resource network that indicates the user associated with the resource application desires assistance from personnel located at the resource location. For example, the user may need assistance from the personnel at the resource location and is unable to and/or does not desire to communicate directly with the personnel. Thus, the computing device can contact the personnel at the resource location to facilitate assisting the user.

The computing device may receive a notification that the resource transaction determined at block 412 is incorrect. For example, in response to transmitting a communication to the user to confirm the resource transaction, the computing device may receive a brain activity signal that indicates the determined resource transaction is not the resource transaction that the user desires to complete. The computing device can determine a different resource transaction based on the received brain activity signal and transmit a notification that indicates a different resource transaction. The computing device may receive an additional brain activity signal that indicates that the different resource transaction is the resource transaction that the user desires to complete.

FIG. 5 illustrates an exemplary system 500 for communicating with a resource distribution device. The system 500 comprises the first networked device 104, a resource network 501 that comprises a communications channel 502 and a resource distribution device 504a. The system 500 also comprises a resource distribution device 504b. A user associated with the first networked device 104 may indicate that the user desires to perform a resource transaction with one of the resource distribution devices 504a,b. For example, the user can be coupled with a brain activity sensor that measures the brain activity of the user to determine one or more thoughts and/or intentions of the user. The first networked device 104 may transmit a communication to the resource network 501 via the communications channel 502. The communications channel 502 may be a wired network and/or a wireless network that facilitates communication among a plurality of devices associated with the resource network 501. For example, the communications channel 502 can be configured to operate as a router to route communications among the plurality of devices on the resource network 501. The first networked device 104 may transmit a communication to the resource network 501 via the communications channel 502. For example, the first networked device 104 may desire to complete a resource transaction with the resource distribution device 504a. The communications channel 502 can facilitate communications between the first networked device 104 and the resource distribution device 504a.

The first networked device 104 can also communicate directly with one or more devices. For example, the first networked device 104 can communicate directly with the resource distribution device 504b. The first networked device 104 can utilize a wireless communications protocol such as Bluetooth, Near Field Communications (NFC), Wi-Fi, cellular, etc. to communicate with the resource distribution device 504b. The first networked device 104 can initiate a resource transfer with the resource distribution device 504b. For example, a user of the first networked device 104 may utilize a brain activity monitor to send thoughts and/or intentions of the user to the resource distribution device 504b to initiate the resource transfer. The resource distribution device 504b may request the location of the first networked device 140 before completing the resource transfer to ensure that the user is proximate to the resource distribution device 504b before proceeding with the transaction.

FIG. 6 illustrates a flowchart of an exemplary method 600. The method 600 can be a computerized method. At block 602, a computing device receives, based on a first brain activity signal from a brain activity measuring device associated with a user, a transmission that indicates a resource account and a password. For example, the computing device can receive an electronic communication and/or transmission from another computing device, such as the first networked device 104, that indicates the user is utilizing a brain activity measuring device. The brain activity measuring device can be configured to communicate with the computing device via a first networked device associated with the user. In one embodiment, the brain activity measuring device is configured to measure electroencephalogram (EEG) signals associated with the user. The computing device can transmit the request for the password in response to determine the user's desire to take one or more actions associated with the resource application. The computing device can transmit the request for the password to confirm that user is authorized to access the resource application and/or a resource account that the user is attempting to access.

At block 604, the computing device determines, based on the first brain activity signal, that the password is associated with the resource account. For example, the computing device can receive an electronic communication from the another computing device that indicates the user's thoughts and/or intentions associated with the password. The electronic communication may indicate a resource account associated with the user and/or the resource application. The computing device can determine, based on the first brain activity signal, that the first brain activity signal indicates the password associated with the resource account. The resource account can be associated with a resource network. The computing device may communicate with the resource network to determine the correct password for the resource account. The computing device can compare the received password with the correct password to determine whether the password is correct.

At block 606, the computing device determines, based on a second brain activity signal, a resource transaction associated with the resource account that the user desires to complete. For example, the computing device can transmit a notification that indicates confirmation that the first brain activity signal indicated the password associated with the resource account and indicates a request for a transaction that the user desires to complete. The computing device may provide a list of possible transactions associated with the resource application and/or the resource account to the another computing device. The computing device can receive, based on transmitting the notification, a second brain activity signal that indicates a resource transaction that the user desires to complete. For example, the computing device can receive an electronic communication from the another computing device that indicates the second brain activity signal associated with the user.

At block 608, the computing device determines an available resource distribution device associated with a resource network that can complete the determined resource transaction that the user desires to complete. For example, there may be a plurality of available resource distribution devices that can perform the requested resource transaction. The computing device may determine a location associated with the user and can determine an available resource distribution device is closest to the user. The computing device can transmit a notification that indicates a location of the available resource distribution device. Additionally, the plurality of available resource distribution devices may have one or more pending transactions. The computing device can determine the one or more pending transactions for each of the plurality of available resource distribution devices. The computing device can also determine an estimated completion time for the requested transaction based on the one or more pending transactions for each of the plurality of available resource distribution devices. The computing device can determine the available resource distribution device with the lowest estimated completion time, as well as the closest to the location of the user. The computing device can receive an electronic communication, such as a brain activity signal, that indicates that the user is unable to access the determined resource distribution device. For example, the user may be wheelchair bound and cannot physically access the resource distribution device. The computing can determine an alternative resource distribution device that the user is able to access and can transmit a notification that indicates a location of the alternative resource distribution device for the user to complete the requested transaction.

At block 610, the computing device transmits, to a networked device associated with the user, a confirmation that the determined resource transaction is accurate and an indication of the available resource distribution device. For example, the computing device can transmit, based on the determined resource transaction that the user desires to complete, a request that the user confirm that the determined resource transaction is the resource transaction that the user desires to complete. The computing device can transmit an electronic communication to the another computing device with an indication of the thought and/or intention that the computing device believes the user desires. As an example, the computing can transmit an electronic communication that requests that the user confirm that the desire to "execute a resource transfer." The computing device may determine that there are two or more resource accounts associated with the user. The computing device can be configured to transmit a notification to the networked device that requests the user to indicate a preferred resource account of the two or more resource accounts. For example, the notification can instruct the user to select the preferred resource account to utilize for the resource transaction. The computing device can receive a brain activity signal associated with the user that indicates the resource account that the user desires to use.

At block 612, the computing device processes, based on a third brain activity signal that indicates the user confirmed the determined resource transaction is accurate, the determined resource transaction. For example, the computing device can receive an electronic communication from the another computing device that indicates the third brain activity signal associated with the user. The third brain activity signal can indicate that the user confirmed that the user desires to "execute a resource transfer."

At block 614, the computing device executes the determined resource transaction based on receiving an indication that the user is proximate to the available resource distribution device. For example, the computing device can receive, via the resource network, a notification that indicates the user is proximate to the available resource distribution device. The computing device may transmit, based on the notification, a transmission to the networked device that requests the user confirm that the user is proximate the available resource distribution device and ready to execute the resource transaction. The computing device can receive a communication that indicates that the user is proximate to the available resource distribution device and is ready to execute the resource transaction. The communication can be received via wireless communication from the networked device or via a communications channel. The computing device can execute the resource transaction based on receiving the confirmation from the user.

FIG. 7 illustrates an exemplary user interface 700 of a device. The first networked device 104 may display on a screen the first resource application 122. The first resource application 122 can facilitate a resource transfer for a user of the first networked device 104. The first resource application 122 can have a first user interface 122a that is associated with calibrating a brain activity measuring device. For example, the user's thoughts and/or intentions may provide data and/or signals that are similar to data and/or signals that are unrelated to the user's thoughts and/or intentions so the brain activity measuring device may need to be calibrated to ensure that the user's thoughts and/or intents are properly determined. As an example, the data and/or signals produced by the brain activity measuring device when the user thinks "resource account" may appear similar to when a user thinks about "a black dog barking." Thus, the first networked device 104 can walk the user through a calibration procedure via the first user interface 122a. As shown, the first user interface 122a prompts the user to picture a resource account and a barking black dog, and to interact with a prompt that indicates whether the user is thinking of the resource account 702 or the barking black dog 704. The user may input a response via an input device such as a touchscreen, keyboard, pointing device, etc. or verbally to a microphone of the first networked device 104. The first resource application 122 can receive the interaction from the user and modify one or more settings associated with the brain activity measuring device so that the user's thoughts and/or intentions are more accurately determined. For example, the first resource application 122 may modify the operational settings so that when the brain activity signal indicates that the user is thinking of a "barking black dog" they are really thinking about a resource account to reduce the chance of a false negative when the user is in fact thinking of a resource account.

The first resource application 122 can have a second user interface 122b. For example, the second user interface 122b can prompt a user of the networked device 104 to picture a password associated with a resource account of the user. The second user interface 122b can provide a first potential password 712 and a second potential password 714 based on the thoughts and/or intentions of the user. The second user interface 122b also includes a prompt that indicates neither of the passwords are correct 716 in case there is an error with the first potential password 712 and second potential password 714. For example, the user may be thinking of the wrong password or the user account may be incorrect. Additionally, the neither are correct prompt 716 can also be used as a security mechanism to purposefully provide false passwords for both the first and second potential passwords 712, 714 to help prevent potential hacking. The user may input a response via an input device such as a touchscreen, keyboard, pointing device, etc. or verbally to a microphone of the first networked device 104. The second user interface 122b may be updated in real time to reflect the current thoughts of the user. For example, if neither of the passwords are correct because the user thought about something other than the password, the second user interface 122b will be updated in real time to indicate the thoughts of the user to help indicate what the first networked device is determining is the users thoughts and/or intentions so that the user may take any corrective action necessary to provide the proper password.

FIG. 8 illustrates a flowchart of an exemplary method 800. The method 800 can be a computerized method. At block 802, the computing device receives from a networked device a transmission that indicates a user desires to calibrate a brain activity measuring device for accessing a resource account. For example, the computing device can receive an electronic communication and/or transmission from another computing device, such as the first networked device 104, that indicates the user is utilizing a brain activity measuring device. The first networked device can send a communication that indicates that the user desires to calibrate the brain activity measuring device. The brain activity measuring device can be configured to communicate with the computing device via a first networked device associated with the user. In one embodiment, the brain activity measuring device is configured to measure electroencephalogram (EEG) signals associated with the user.

At block 804, the computing device receives descriptive information associated with the user that indicates a calibration procedure appropriate for the user. For example, the user can provide descriptive information to the computing device via the first networked device. Any descriptive information received can be encrypted and/or destroyed after calibration of the brain activity measuring device to protect that data. In some embodiments, descriptive information associated with the user is not utilized. The computing device can determine, based on the descriptive information, a potential calibration procedure from a plurality of potential calibration procedures. For example, the descriptive information and/or properties can indicate how old a user is, a location, a language associated with the user, or any pertinent information that can facilitate properly calibrating the brain activity measuring device. A personalized account can be generated that is associated with each user to store the descriptive information and/or properties of the user. The personalized account can be utilized to determine a proper calibration procedure, as well as improve the functioning of the brain waive monitoring device. The computing device may determine, based on one or more brain activity signals, that the potential calibration procedure is not appropriate for the user. The computing device may determine, based on the descriptive information and the potential calibration procedure, a calibration procedure that is more appropriate for the user. For example, the user may be a native Spanish speaker, and the original calibration procedure was in English, which may cause difficult for the native Spanish speaker to properly calibrate the brain activity measuring device. Thus, the computing device may provide a calibration procedure in Spanish to help the user calibrate the brain activity measuring device.

At block 806, the computing device transmits to the networked device instructions for a first step in the calibration procedure for the user to execute. The first step in the calibration procedure can comprise instructing the user to concentrate on imaging a typical resource transaction associated with a resource account. The first step in the calibration procedure can also comprise instructing the user to concentrate on the password associated with the resource account.

At block 808, the computing device receives, based on the first step in the calibration procedure, a first brain activity signal associated with the user. For example, the computing device can receive an electronic communication and/or transmission from another computing device, such as the first networked device 104, that indicates the user's response to the first step in the calibration procedure.

At block 810, the computing device modifies, based on the first brain activity signal, one or more settings associated with the brain activity measuring device to improve determining brain activity signals associated with the user. The computing device can configure the brain activity measuring device to identify the first brain activity signal as indicating the typical resource transaction associated with the resource account.

At block 812, the computing device transmits to the networked device a second step in the calibration procedure based on the one or more modified settings to verify the modification improved determining brain activity signals associated with the user. The second step in the calibration procedure can comprise instructing the user to concentrate on a thought that can produce a similar brain activity signal as the typical resource transaction associated with the resource account as discussed with regards to the first step in the calibration procedure. However, the thought in the second step in the calibration procedure is irrelevant to the typical resource transaction. The second step in the calibration procedure can also comprise instructing the user to concentrate on a thought that can produce a similar brain activity signal as the password associated with the resource account.

At block 814, the computing device stores, based on receiving a second brain activity signal associated with the second step in the calibration procedure that verify the one or more modified settings improved determining brain activity signals associated with the user, the one or more modified settings. The computing device can configure the brain activity measuring device to identify the second brain activity signal as indicating an irrelevant thought that should be ignored. In another embodiment, the computing device can configure the brain activity measuring device to identify the second brain activity signal as indicating the typical resource transaction associated with the resource account. In a further embodiment, the computing device can configure the brain activity measuring device to identify the second brain activity signal as indicating the password associated with the resource account.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, and the like), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational steps to be performed on the computer or other programmable apparatus to produce a computer-implemented process such that the code portions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system for calibration of a brain activity measuring device for detection of specific brainwave patterns, the system comprising:

at least one memory device;

at least one communication device connected to a communications network;

at least one processing device operatively coupled to the at least one memory device; and a module stored in the at least one memory device comprising executable instructions that when executed by the at least one processing device, cause the at least one processing device to:

receive from a networked device a transmission that indicates a user desires to calibrate a brain activity measuring device for accessing a resource account;

receive descriptive information associated with the user that indicates a calibration procedure appropriate for the user;

transmit to the networked device instructions for a first step in the calibration procedure for the user to execute;

receive, based on the first step in the calibration procedure, a first brain activity signal associated with the user;

modify, based on the first brain activity signal, one or more settings associated with the brain activity measuring device to improve determining brain activity signals associated with the user;

transmit to the networked device a second step in the calibration procedure based on the one or more modified settings to verify the modification improved determining brain activity signals associated with the user; and store, based on receiving a second brain activity signal associated with the second step in the calibration procedure that verify the one or more modified settings improved determining brain activity signals associated with the user, the one or more modified settings.

2. The system of claim 1, wherein the executable instructions further cause the at least one processing device to:
   determine, based on the descriptive information, a potential calibration procedure from a plurality of potential calibration procedures;
   determine, based on the first brain activity signal, that the potential calibration procedure is not appropriate for the user; and
   determine, based on the descriptive information and the potential calibration procedure, the calibration procedure for the user to execute.

3. The system of claim 1, wherein the first step in the calibration procedure comprises instructing the user to concentrate on imaging a typical resource transaction associated with a resource account, and wherein the second step in the calibration procedure comprises instructing the user to concentrate on a thought that can produce a similar brain activity signal as the typical resource transaction associated with the resource account, wherein the thought is irrelevant to the typical resource transaction.

4. The system of claim 3, wherein modifying the one or more settings associated with the brain activity measuring device further comprises:
   configuring the brain activity measuring device to identify the first brain activity signal as indicating the typical resource transaction associated with the resource account; and
   configuring the brain activity measuring device to identify the second brain activity signal as indicating an irrelevant thought that should be ignored.

5. The system of claim 3, wherein modifying the one or more settings associated with the brain activity measuring device further comprises:
   configuring the brain activity measuring device to identify the first brain activity signal as indicating the typical resource transaction associated with the resource account; and
   configuring the brain activity measuring device to identify the second brain activity signal as indicating the typical resource transaction associated with the resource account.

6. The system of claim 1, wherein the executable instructions further cause the at least one processing device to receive a password associated with the resource account, wherein the first step in the calibration procedure comprises instructing the user to concentrate on the password associated with the resource account, and wherein the second step in the calibration procedure comprises instructing the user to concentrate on a thought that can produce a similar brain activity signal as the password associated with the resource account.

7. The system of claim 6, wherein modifying the one or more settings associated with the brain activity measuring device further comprises:
   configuring the brain activity measuring device to identify the first brain activity signal as indicating the password associated with the resource account; and
   configuring the brain activity measuring device to identify the second brain activity signal as indicating the password associated with the resource account.

8. A computer program product for calibration of a brain activity measuring device for detection of specific brainwave patterns, the computer program product comprising a non-transitory computer-readable storage medium having computer-executable instructions to:
   receive from a networked device a transmission that indicates a user desires to calibrate a brain activity measuring device for accessing a resource account;
   receive descriptive information associated with the user that indicates a calibration procedure appropriate for the user;
   transmit to the networked device instructions for a first step in the calibration procedure for the user to execute;
   receive, based on the first step in the calibration procedure, a first brain activity signal associated with the user;
   modify, based on the first brain activity signal, one or more settings associated with the brain activity measuring device to improve determining brain activity signals associated with the user;
   transmit to the networked device a second step in the calibration procedure based on the one or more modified settings to verify the modification improved determining brain activity signals associated with the user; and
   store, based on receiving a second brain activity signal associated with the second step in the calibration procedure that verify the one or more modified settings improved determining brain activity signals associated with the user, the one or more modified settings.

9. The computer program product of claim 8, wherein the computer program product further comprises computer-executable instructions to:
   determine, based on the descriptive information, a potential calibration procedure from a plurality of potential calibration procedures;
   determine, based on the first brain activity signal, that the potential calibration procedure is not appropriate for the user; and
   determine, based on the descriptive information and the potential calibration procedure, the calibration procedure for the user to execute.

10. The computer program product of claim 8, wherein the first step in the calibration procedure comprises instructing the user to concentrate on imaging a typical resource transaction associated with a resource account, and wherein the second step in the calibration procedure comprises instructing the user to concentrate on a thought that can produce a similar brain activity signal as the typical resource transaction associated with the resource account, wherein the thought is irrelevant to the typical resource transaction.

11. The computer program product of claim 10, wherein modifying the one or more settings associated with the brain activity measuring device further comprises:
   configuring the brain activity measuring device to identify the first brain activity signal as indicating the typical resource transaction associated with the resource account; and
   configuring the brain activity measuring device to identify the second brain activity signal as indicating an irrelevant thought that should be ignored.

12. The computer program product of claim 10, wherein modifying the one or more settings associated with the brain activity measuring device further comprises:
   configuring the brain activity measuring device to identify the first brain activity signal as indicating the typical resource transaction associated with the resource account; and configuring the brain activity measuring device to identify the second brain activity signal as indicating the typical resource transaction associated with the resource account.

13. The computer program product of claim 8, wherein the computer program product further comprises computer-executable instructions to receive a password associated with the resource account, wherein the first step in the calibration procedure comprises instructing the user to concentrate on the password associated with the resource account, and wherein the second step in the calibration procedure comprises instructing the user to concentrate on a thought that can produce a similar brain activity signal as the password associated with the resource account.

14. The computer program product of claim 13, wherein modifying the one or more settings associated with the brain activity measuring device further comprises:
configuring the brain activity measuring device to identify the first brain activity signal as indicating the password associated with the resource account; and
configuring the brain activity measuring device to identify the second brain activity signal as indicating the password associated with the resource account.

15. A computerized method for calibration of a brain activity measuring device for detection of specific brainwave patterns, the computerized method comprising:
receiving from a networked device a transmission that indicates a user desires to calibrate a brain activity measuring device for accessing a resource account;
receiving descriptive information associated with the user that indicates a calibration procedure appropriate for the user;
transmitting to the networked device instructions for a first step in the calibration procedure for the user to execute;
receiving, based on the first step in the calibration procedure, a first brain activity signal associated with the user;
modifying, based on the first brain activity signal, one or more settings associated with the brain activity measuring device to improve determining brain activity signals associated with the user;
transmitting to the networked device a second step in the calibration procedure based on the one or more modified settings to verify the modification improved determining brain activity signals associated with the user; and
storing, based on receiving a second brain activity signal associated with the second step in the calibration procedure that verify the one or more modified settings improved determining brain activity signals associated with the user, the one or more modified settings.

16. The computerized method of claim 15, further comprising:
determining, based on the descriptive information, a potential calibration procedure from a plurality of potential calibration procedures;
determining, based on the first brain activity signal, that the potential calibration procedure is not appropriate for the user; and
determining, based on the descriptive information and the potential calibration procedure, the calibration procedure for the user to execute.

17. The computerized method of claim 15, wherein the first step in the calibration procedure comprises instructing the user to concentrate on imaging a typical resource transaction associated with a resource account, and wherein the second step in the calibration procedure comprises instructing the user to concentrate on a thought that can produce a similar brain activity signal as the typical resource transaction associated with the resource account, wherein the thought is irrelevant to the typical resource transaction.

18. The computerized method of claim 17, wherein modifying the one or more settings associated with the brain activity measuring device further comprises:
configuring the brain activity measuring device to identify the first brain activity signal as indicating the typical resource transaction associated with the resource account; and
configuring the brain activity measuring device to identify the second brain activity signal as indicating an irrelevant thought that should be ignored.

19. The computerized method of claim 17, wherein modifying the one or more settings associated with the brain activity measuring device further comprises:
configuring the brain activity measuring device to identify the first brain activity signal as indicating the typical resource transaction associated with the resource account; and
configuring the brain activity measuring device to identify the second brain activity signal as indicating the typical resource transaction associated with the resource account.

20. The computerized method of claim 15, further comprising:
receiving a password associated with the resource account, wherein the first step in the calibration procedure comprises instructing the user to concentrate on the password associated with the resource account, and wherein the second step in the calibration procedure comprises instructing the user to concentrate on a thought that can produce a similar brain activity signal as the password associated with the resource account;
configuring the brain activity measuring device to identify the first brain activity signal as indicating the password associated with the resource account; and
configuring the brain activity measuring device to identify the second brain activity signal as indicating the password associated with the resource account.

* * * * *